(12) United States Patent  (10) Patent No.: US 8,287,494 B2
Ma  (45) Date of Patent: Oct. 16, 2012

(54) INTRAVITREAL INJECTION DEVICES AND METHODS OF INJECTING A SUBSTANCE INTO THE VITREOUS CHAMBER OF THE EYE

(76) Inventor: Colin Ma, Portland, OR (US)

( * ) Notice: Subject to any disclaimer, the term of this patent is extended or adjusted under 35 U.S.C. 154(b) by 286 days.

(21) Appl. No.: 12/729,488

(22) Filed: Mar. 23, 2010

(65) Prior Publication Data

US 2010/0241102 A1 Sep. 23, 2010

Related U.S. Application Data

(60) Provisional application No. 61/162,445, filed on Mar. 23, 2009.

(51) Int. Cl.
*A61M 35/00* (2006.01)
*A61M 1/00* (2006.01)
(52) U.S. Cl. ........................................ 604/151; 604/294
(58) Field of Classification Search .................. 604/294, 604/300–302, 521, 151
See application file for complete search history.

(56) References Cited

U.S. PATENT DOCUMENTS

| | | | |
|---|---|---|---|
| 5,372,585 A | 12/1994 | Tiefenbrun et al. | |
| 5,372,595 A | 12/1994 | Gaasterland et al. | |
| 5,540,657 A | 7/1996 | Kurjan et al. | |
| 5,632,984 A | 5/1997 | Wong et al. | |
| 5,770,589 A | 6/1998 | Billson et al. | |
| 6,309,374 B1 | 10/2001 | Hecker et al. | |
| 6,397,849 B1 | 6/2002 | Bowman et al. | |
| 6,620,137 B2 | 9/2003 | Kirchhofer et al. | |
| 6,656,197 B1 | 12/2003 | LaHaye | |
| 7,137,967 B2 | 11/2006 | Nemoto | |
| 7,297,136 B2 | 11/2007 | Wyrick | |
| 2001/0049496 A1 | 12/2001 | Kirchhofer et al. | |
| 2003/0060763 A1 | 3/2003 | Penfold et al. | |
| 2007/0005016 A1 | 1/2007 | Williams | |
| 2007/0129686 A1 | 6/2007 | Daily et al. | |
| 2007/0142787 A1 | 6/2007 | Scherer | |
| 2008/0154204 A1 | 6/2008 | Varner et al. | |
| 2008/0243095 A1 | 10/2008 | Kaiser et al. | |

*Primary Examiner* — Kevin C Sirmons
*Assistant Examiner* — Bradley Osinski
(74) *Attorney, Agent, or Firm* — Dascenzo Intellectual Property Law, P.C.

(57) ABSTRACT

Intravitreal injection devices include an injection assembly adapted to receive an injector, and an alignment guide adapted to facilitate placement of the injector relative to a patient's eye for injecting an injectant therein. The injection assembly, in response to a user input, is adapted to automatically and sequentially first, translate the injector into the patient's eye, and then second, dispense the injectant from the injector. In some embodiments the injector is a typical syringe. Some embodiments are adapted to receive syringes having different configurations. Methods of injecting an injectant into a patient's eye are also provided.

24 Claims, 7 Drawing Sheets

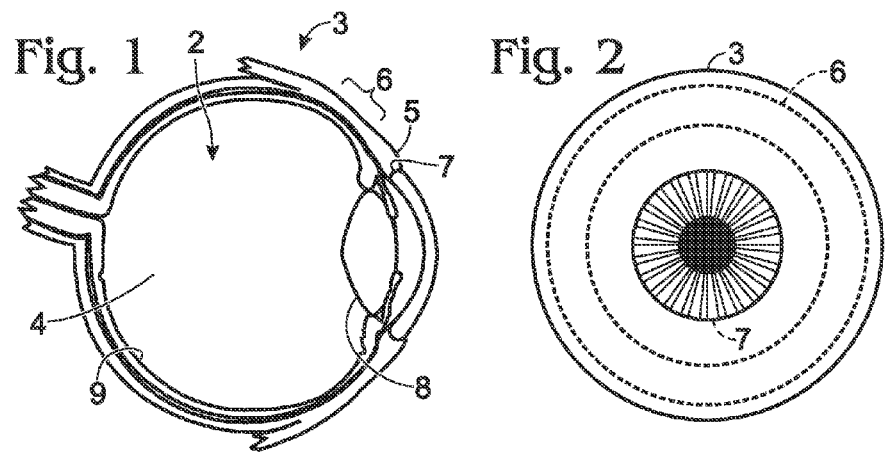
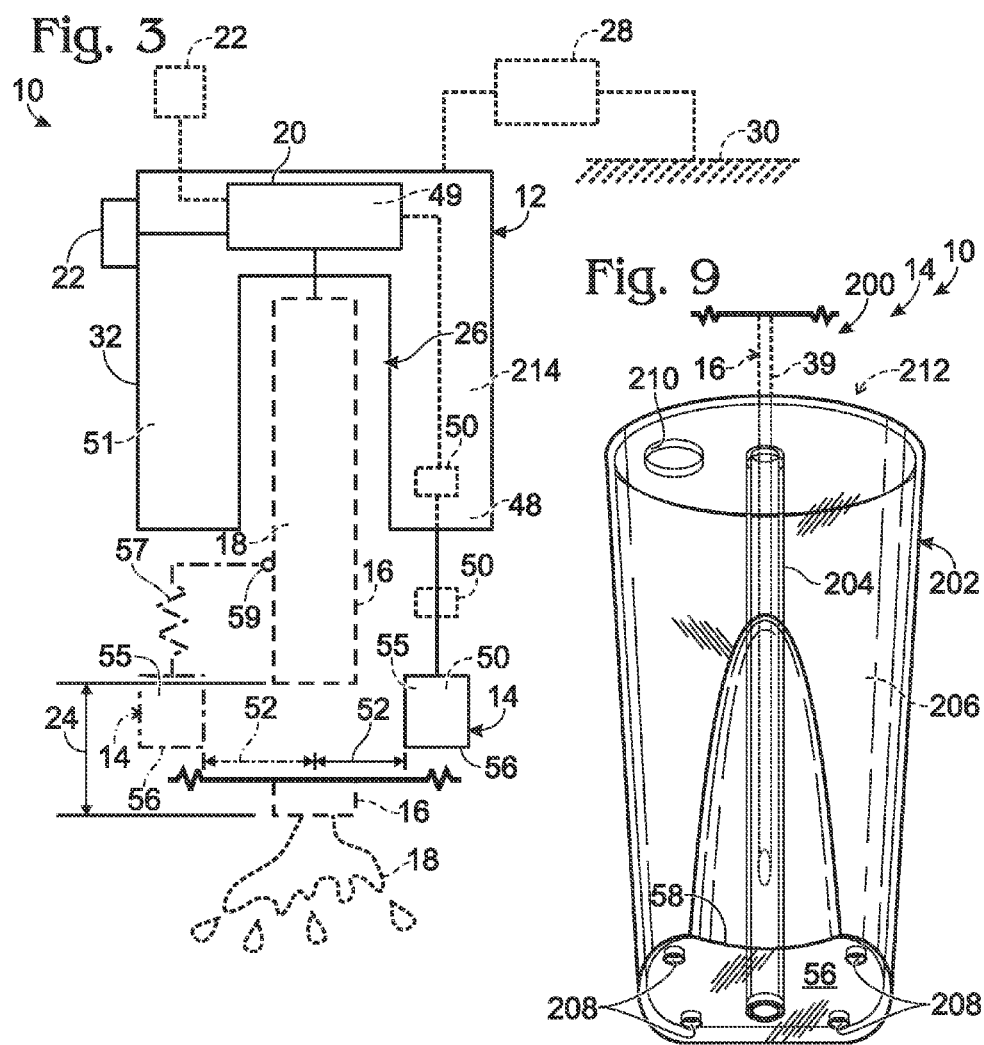

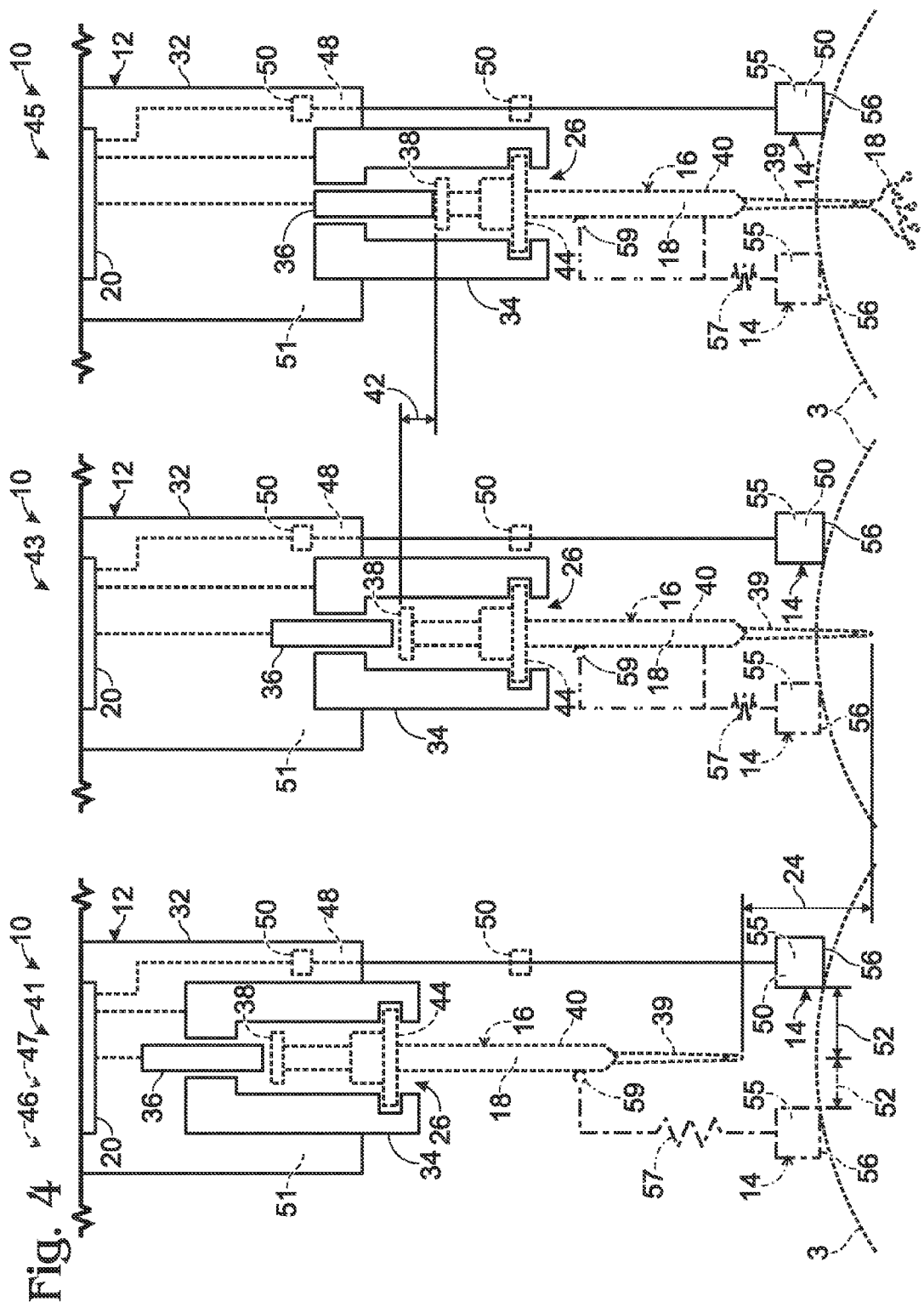

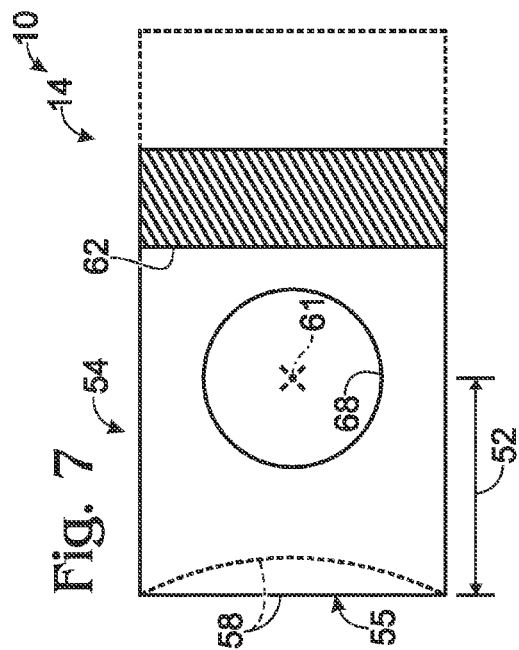
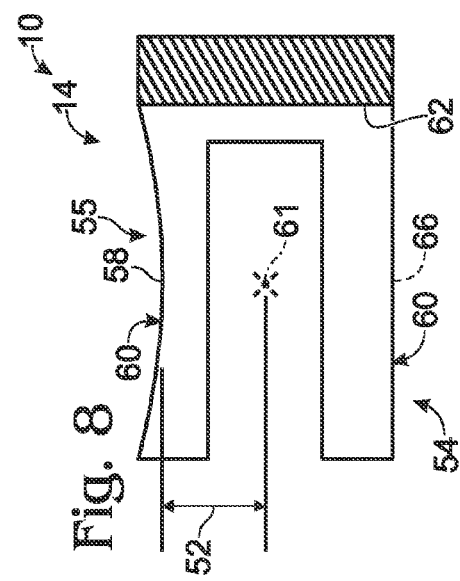
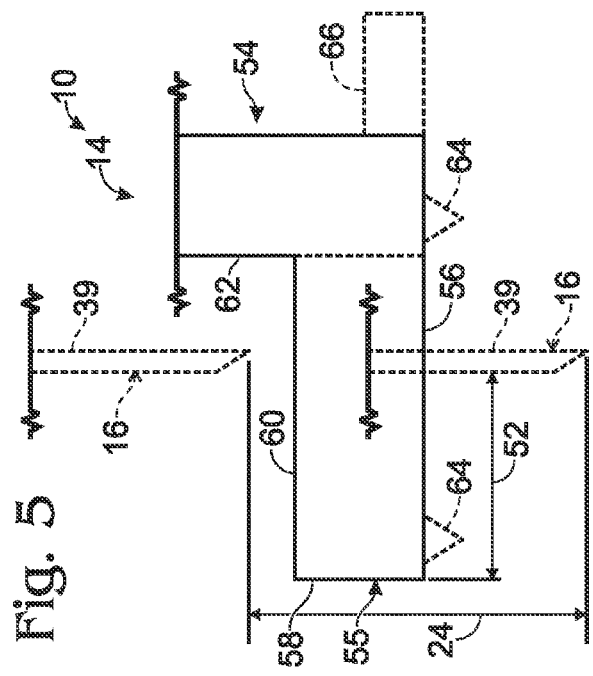
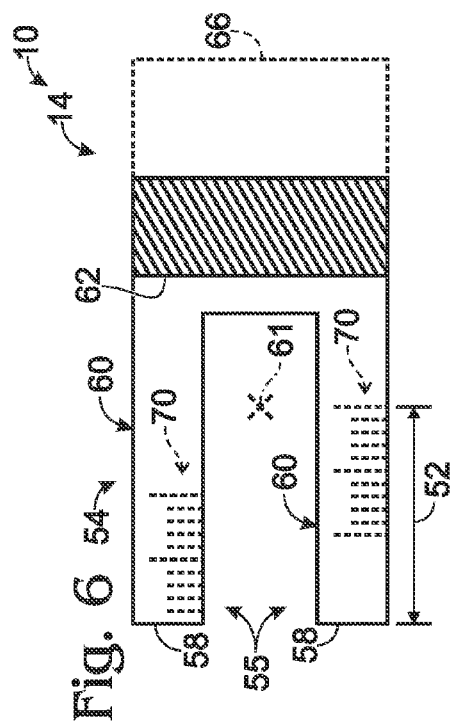

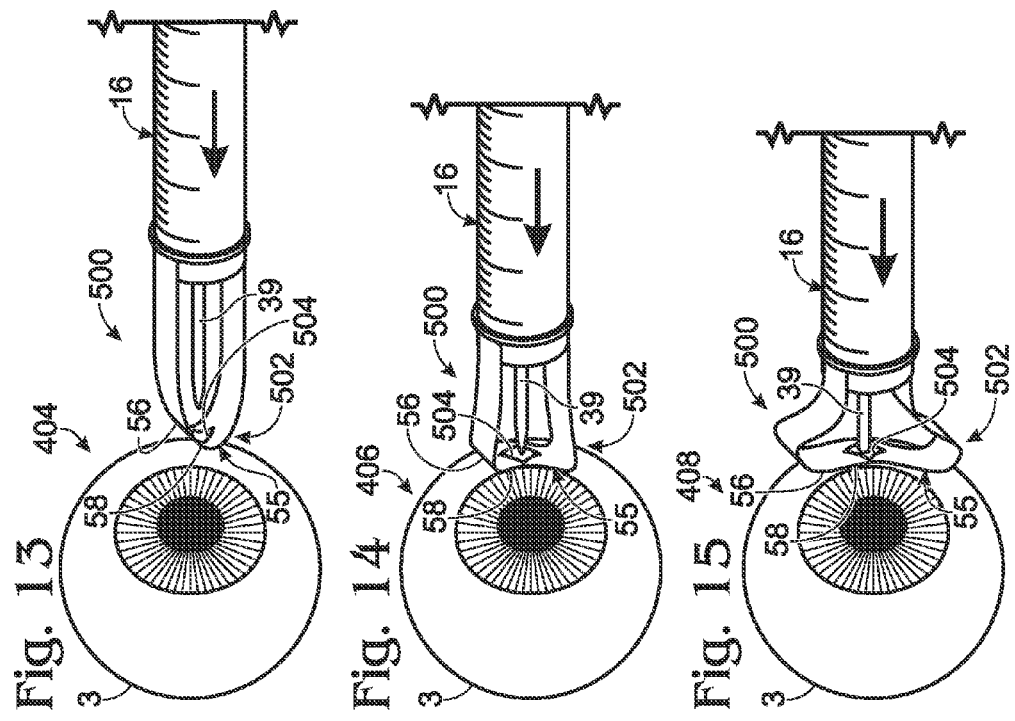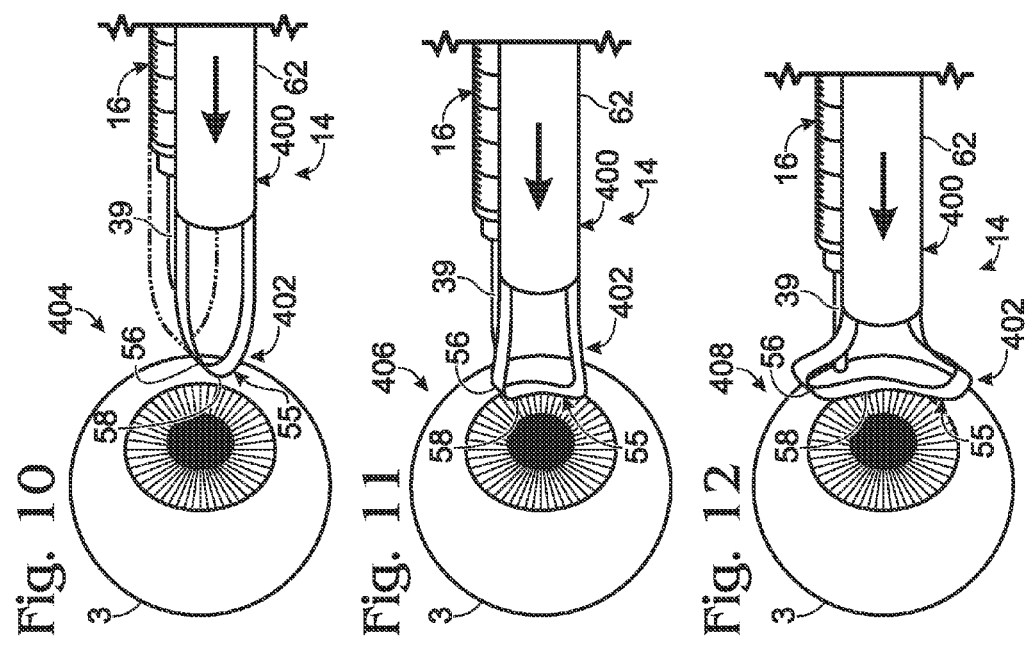

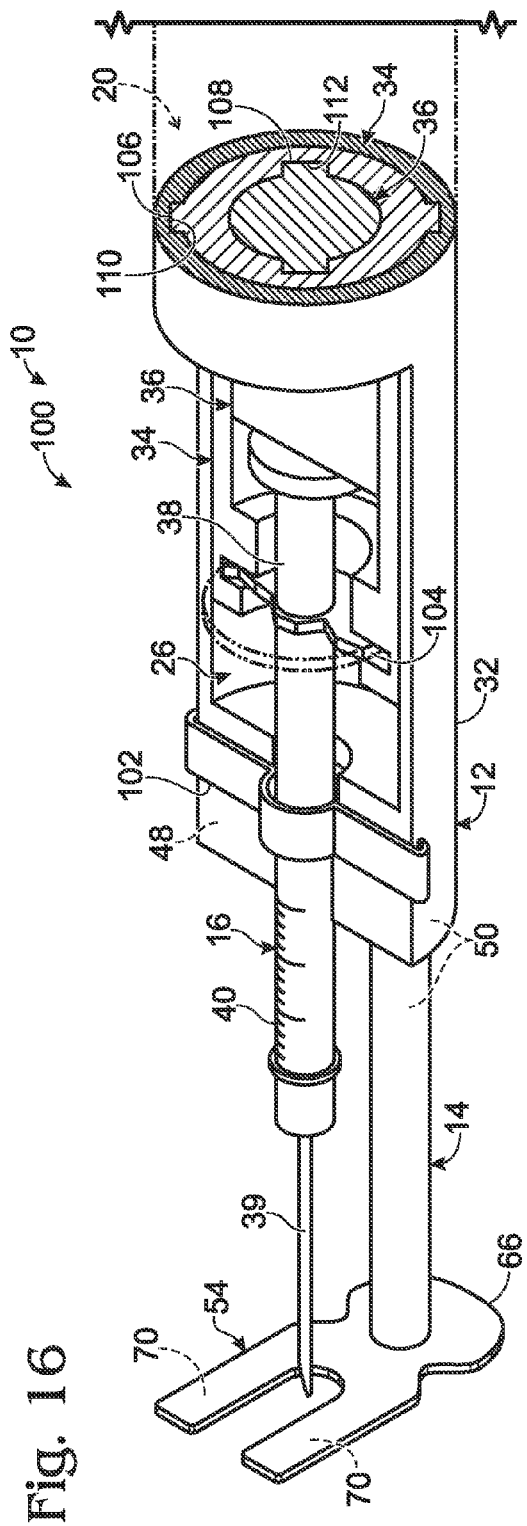
Fig. 16
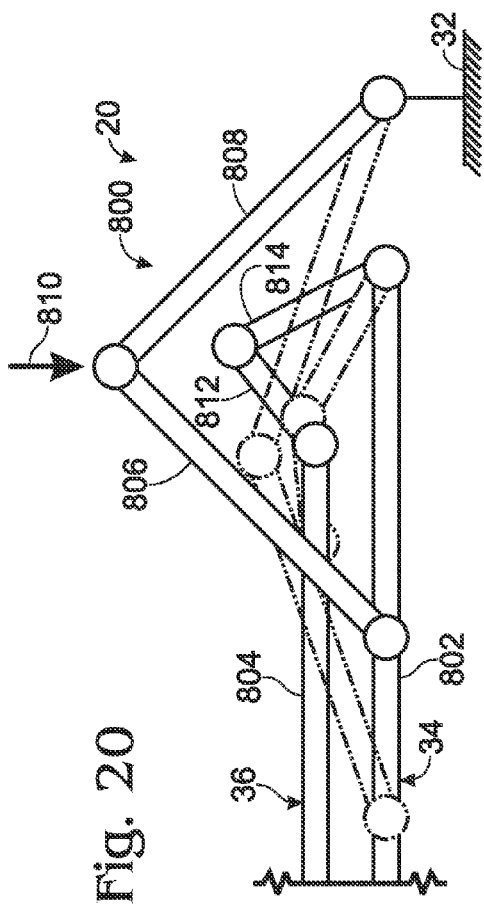
Fig. 17
Fig. 20

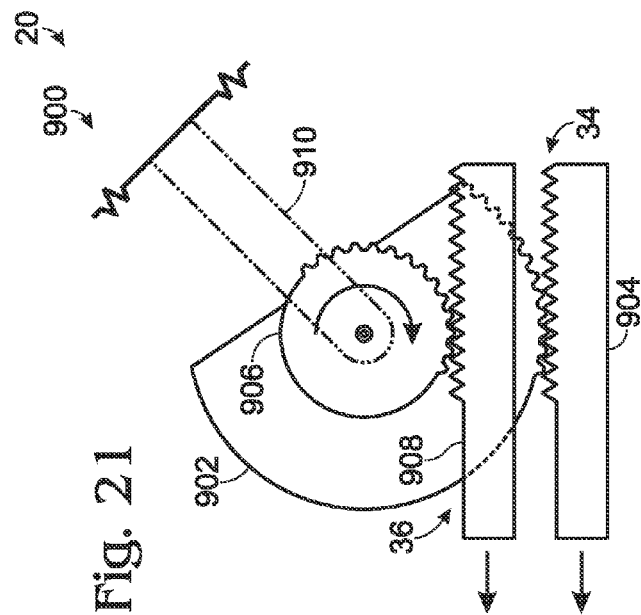
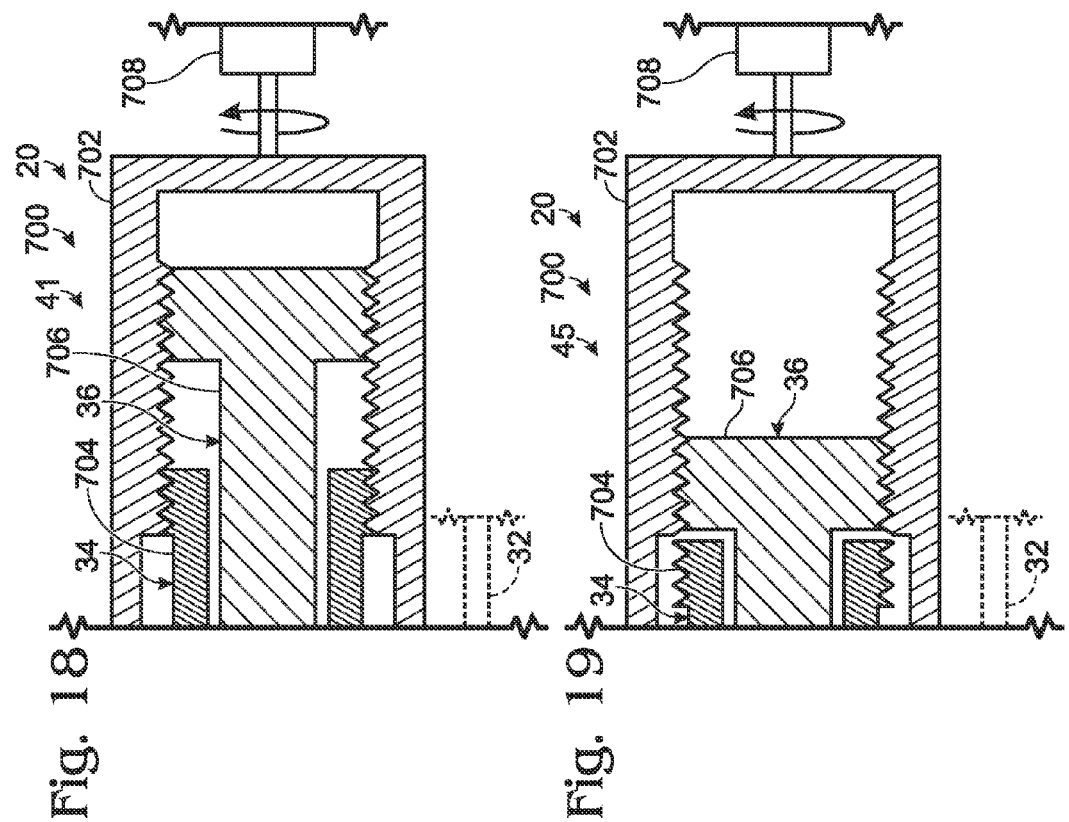

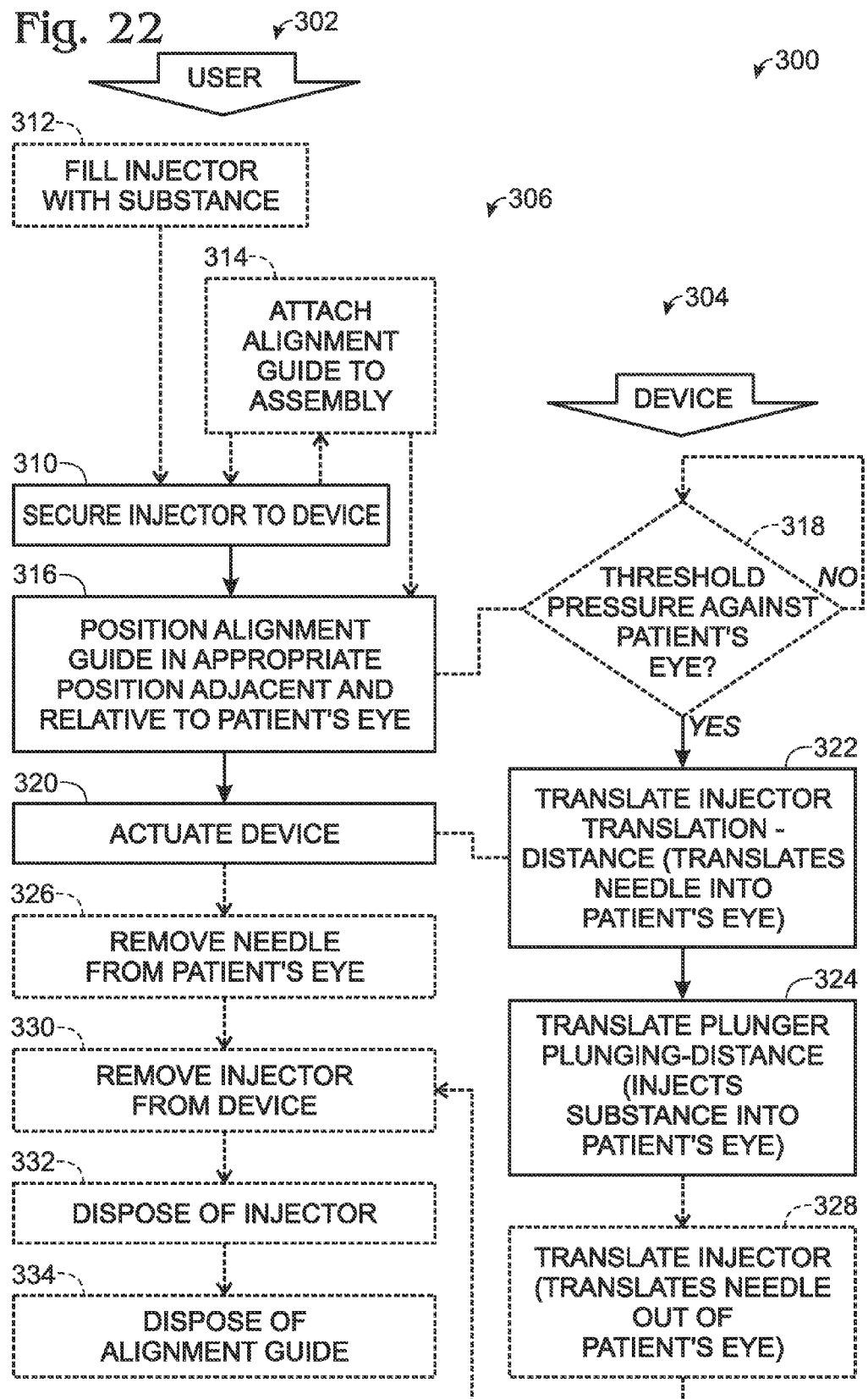

INTRAVITREAL INJECTION DEVICES AND METHODS OF INJECTING A SUBSTANCE INTO THE VITREOUS CHAMBER OF THE EYE

RELATED APPLICATION

This application claims priority to U.S. Provisional Patent Application Ser. No. 61/162,445, which is entitled "INTRAVITREAL INJECTION DEVICES AND METHODS OF INJECTING A SUBSTANCE INTO THE VITREOUS CHAMBER OF THE EYE," was filed on Mar. 23, 2009, and the complete disclosure of which is hereby incorporated by reference.

FIELD OF THE DISCLOSURE

The present disclosure is directed generally to intravitreal injection devices and methods of injecting a substance into the vitreous chamber of the eye, and more particularly to intravitreal injection devices that include a guide for precision alignment and activation of an injector for injecting a substance into the vitreous chamber of the eye and to methods of using such intravitreal injection devices.

BACKGROUND OF THE DISCLOSURE

Age-related macular degeneration affects approximately 20% of those over the age of 55. In many patients, the disease causes blood vessels within the eye to grow, bleed, and then scar, resulting in severe and disabling loss of vision. Conventional treatment currently consists of regular injection into the eye, every 4-6 weeks, of drugs, such as LUCENTIS® or AVASTIN®. Such injections must be made precisely to avoid damage to various parts of the eye. In reference to FIG. 1, the drug should be delivered into the vitreous cavity, or chamber, 2 of a patient's eye 3, which is filled with the vitreous humor 4—a clear gel-like substance. To enter the vitreous cavity safely, the needle of a syringe must pass through the sclera (the white of the eye) 5 via the pars plana 6. The pars plana is a ring-shaped zone, which is defined by two imaginary circles that are situated about three and five millimeters, respectively, outside the edge of the cornea 7 of eye 3, as schematically illustrated in FIG. 2. Referring again to FIG. 1, a needle that is inserted through the pars plana and directed appropriately will pass between the lens 8 and the retina 9, thereby avoiding injury to both structures. Currently, to make these injections, retina specialists use one hand to hold the patient's eye open and steady. The other hand is then used to, first, insert the needle of a syringe into the appropriate location at an appropriate angle and to an appropriate depth in the eye, and then second, press the plunger of the syringe to inject the drug into the eye. Finally, the needle is withdrawn from the eye.

Injection of a substance into and/or extraction of a substance from an eye may be performed for various reasons, including, but not limited to, one or more of the treatment of macular degeneration, diabetic retinopathy, uveitis, infections, inflammations, etc.

SUMMARY OF THE DISCLOSURE

The present disclosure is directed to intravitreal injection devices that include an injection assembly that is adapted to receive an injector, and an alignment guide that is adapted to facilitate placement of the injector relative to a patient's eye for injecting an injectant therein. Also disclosed are methods of injecting a substance into a patient's eye by an intravitreal injection device and methods of injecting a substance into a patient's eye utilizing an intravitreal injection device.

Intravitreal injection devices according to the present disclosure are configured to automatically and sequentially first, translate an injector into a patient's eye, and then second, dispense an injectant from the injector. In some embodiments, the injector is a conventional syringe. Some embodiments are adapted to receive syringes having different configurations. Some embodiments are further configured to automatically retract the injector from the patient's eye after dispensing the injectant therein.

Methods of injecting a substance into a patient's eye by an intravitreal injection device include receiving an injector, engaging a surface of the patient's eye, translating the injector, and dispensing an injectant from the injector.

Methods of injecting a substance into a patient's eye utilizing an intravitreal injection device (e.g., by a physician or a medical technician) include securing an injector to an intravitreal injection device, positioning the device adjacent to the patient's eye, aligning an alignment guide of the device with a visible aspect of the patient's eye, positioning the device so that the alignment guide engages the surface of the patient's eye, and actuating the device so that it automatically and sequentially first, translates the injector into the patient's eye and then second, dispenses an injectant into the patient's eye.

BRIEF DESCRIPTION OF THE DRAWINGS

FIG. 1 is a side cross-sectional diagram of a typical human eye.

FIG. 2 is a front diagram of a typical human eye, schematically illustrating the location of the pars plana.

FIG. 3 is a schematic illustration representing examples of intravitreal injection devices according to the present disclosure, shown with an associated injector.

FIG. 4 is a schematic illustration of a portion of intravitreal injection devices according to the present disclosure, shown together with a patient's eye and an associated injector in the form of a syringe, and sequentially showing (from left to right) the intravitreal injection devices in an injector-receipt configuration, a translated configuration, and a dispensed configuration.

FIG. 5 is a schematic side view illustration representing illustrative, non-exclusive examples of a portion of an alignment guide of intravitreal injection devices according to the present disclosure, shown together with a portion of an associated syringe.

FIG. 6 is a schematic top view illustration representing illustrative, non-exclusive examples of a portion of an alignment guide of intravitreal injection devices according to the present disclosure.

FIG. 7 is a schematic top view illustration representing illustrative, non-exclusive examples of a portion of an alignment guide of intravitreal injection devices according to the present disclosure.

FIG. 8 is a schematic top view illustration representing illustrative, non-exclusive examples of a portion of an alignment guide of intravitreal injection devices according to the present disclosure.

FIG. 9 is an isometric view of a portion of an illustrative, non-exclusive example of an alignment guide of intravitreal injection devices according to the present disclosure, shown together with a portion of an associated syringe.

FIG. 10 is an isometric view of a portion of an illustrative, non-exclusive example of an alignment guide of intravitreal injection devices according to the present disclosure, shown together with a patient's eye and with a portion of an associated syringe spaced away from the patient's eye, and with the alignment guide in an unflexed configuration.

FIG. 11 is an isometric view of the portion of the alignment guide of FIG. 10, shown together with a portion of an associated syringe having been translated toward the patient's eye relative to the position illustrated in FIG. 10, and with the alignment guide partially conformed to the surface of the patient's eye.

FIG. 12 is an isometric view of the portion of the alignment guide of FIG. 10, shown together with a portion of an associated syringe, and with the needle of the syringe having pierced into the patient's eye, and with the alignment guide conformed to the surface of the patient's eye to an extent greater than as shown in FIG. 11.

FIG. 13 is an isometric view of another illustrative, non-exclusive example of an alignment guide of intravitreal injection devices according to the present disclosure, the alignment guide coupled to an associated syringe, shown together with a patient's eye, and with the alignment guide in an unflexed configuration.

FIG. 14 is an isometric view of the alignment guide and syringe of FIG. 13, shown with the syringe having been translated toward the patient's eye relative to the position illustrated in FIG. 13, and with the alignment guide partially conformed to the surface of the patient's eye.

FIG. 15 is an isometric view of the alignment guide and syringe of FIG. 13, shown with the needle of the syringe having pierced into the patient's eye, and with the alignment guide conformed to the surface of the patient's eye to an extent greater than as shown in FIG. 14.

FIG. 16 is a somewhat less schematic partial cross-sectional isometric view of a portion of an illustrative, non-exclusive example of an intravitreal injection device according to the present disclosure, shown together with an associated syringe.

FIG. 17 is a somewhat schematic side view of a portion of an illustrative, non-exclusive example of an activator of intravitreal injection devices according to the present disclosure.

FIG. 18 is a somewhat schematic side view of a portion of another illustrative, non-exclusive example of an activator of intravitreal injection devices according to the present disclosure, shown with the intravitreal injection device in an injector-receipt configuration.

FIG. 19 is a somewhat schematic side view of the portion of the activator of FIG. 18, shown with the intravitreal injection device in a dispensed configuration.

FIG. 20 is a somewhat schematic side view of a portion of another illustrative, non-exclusive example of an activator of intravitreal injection devices according to the present disclosure, shown with the intravitreal injection device in an injector-receipt configuration and in a dispensed configuration.

FIG. 21 is a somewhat schematic side view of a portion of another illustrative, non-exclusive example of an activator of intravitreal injection devices according to the present disclosure, with the intravitreal injection device in an injector-receipt configuration FIG. 22 is a flow chart schematically illustrating illustrative, non-exclusive examples of methods according to the present disclosure, the methods including steps performed by a user and/or by an intravitreal injection device according to the present disclosure.

DETAILED DESCRIPTION AND BEST MODE OF THE DISCLOSURE

Intravitreal injection devices according to the present disclosure are schematically illustrated in FIGS. 3-4 and are indicated generally at 10. Intravitreal injection devices according to the present disclosure are designed to inject a substance, such as a pharmaceutical, into the vitreous chamber of a patient's eye. This substance may additionally or alternatively be referred to herein as an injectant, a medicant, and/or a composition without departing from the scope of the present disclosure. More specifically, intravitreal injection devices according to the present disclosure are designed to permit a physician, medical technician, or other user to properly position and insert a portion of an injector, such as a needle of a syringe, into a patient's eye and then to dispense an injectant 18, such as a pharmaceutical, from the injector into the vitreous chamber without damaging the eye, for example, without touching and/or damaging delicate structure of the patient's eye, including (but not limited to) the eye's lens or retina.

Illustrative, non-exclusive examples of intravitreal injection devices according to the present disclosure, and related methods, may be designed to automatically and sequentially first, insert a dispensing conduit of an injector (e.g., a needle of a syringe) into a patient's eye and then second, dispense an injectant through the dispensing conduit into the patient's eye. Intravitreal injection devices and related methods may be adapted to provide sequentially both of these steps, or movements, in response to a single activation of, or user input to, the device, such as by a physician, medical technician, or other user. Intravitreal injection devices 10 according to the present disclosure are not required to be used only by, and methods according to the present disclosure are not required to be performed only by, a physician or a medical technician, but rather may be used by any suitable user. In some situations, this user may be a physician, or medical technician, but this is not an exclusive group of potential users. Moreover, although not required, devices and methods according to the present disclosure may be implemented by a single user without the aid of an assistant, and in some embodiments may be performed in a one-handed manner by this user.

Intravitreal injection devices 10 according to the present disclosure include at least an injection assembly 12 and an alignment guide 14, and may further include a stabilization assembly 28, as schematically illustrated in FIG. 3. Injection assembly 12 may additionally or alternatively be referred to as an injector holder, an activator assembly, and/or an injector holder and activator assembly 12.

Injection assembly 12 is adapted to selectively receive and secure thereto an injector 16 in a defined orientation relative to the injection assembly. Additionally, assembly 12 may be further adapted to selectively release the injector from the injection assembly, for example, for disposal thereof, as discussed herein. Illustrative, non-exclusive examples of injectors 16 include pre-filled syringes with a single dose of a pharmaceutical. For example, syringes may be pre-filled by a pharmacist, by a pharmaceutical supplier, or by the physician or medical technician performing the procedure. Other injectors 16 may include syringes that are filled with a dose of a pharmaceutical by a physician or medical technician relatively immediately before, or just prior to, injection of the pharmaceutical into the patient's eye. Other types and configurations of injectors are also within the scope of the present disclosure, including injectors that are configured to inject a liquid substance, a gaseous substance, and/or a solid substance, such as a solid pellet of pharmaceutical, for example, to enable a timed release of the pharmaceutical within the patient's eye. An illustrative, non-exclusive example of a gaseous substance that may be used with devices and injectors according to the present disclosure includes sulfur hexafluoride, for example, for the treatment of a detached retina, but other gaseous substances may be utilized without departing from the scope of the present disclosure. Additionally or alternatively, injection assemblies 12 according to the present disclosure may be adapted to selectively receive and secure thereto an extraction device, or extractor, such as may be used to extract a substance from the vitreous chamber of a patient's eye. Although referred to herein as an injector 16, devices 10 according to the present disclosure also may be configured for use with an extraction device in place of an injector 16. Accordingly, the subsequent discussion will refer to injectors 16, but it is within the scope of the present disclosure to apply portions of the following discussion to an extractor (16).

As schematically illustrated in FIG. 3, injection assembly 12 defines an injector receiving region 26, which is adapted to receive an injector 16, and a housing 32, which is adapted to be selectively grasped by a user and manipulated to position the injector adjacent to a patient's eye. Injection assembly 12 further includes an activator 20 that is coupled to, or otherwise supported by or connected to, the housing, and a user actuation mechanism 22 that is supported by, or otherwise coupled to or connected to, the housing. Housing 32 may be sized or otherwise designed and adapted for engagement by a user, such as by a physician or medical technician, for appropriate manual positioning of a device 10 adjacent a patient's eye. In some embodiments, and although not required, the housing may be configured for manipulation by a user using only one hand. The user actuation mechanism is adapted to actuate, or activate, the activator 20 upon engagement by a user. In embodiments in which the user actuation mechanism is coupled directly to the housing, a user may both manipulate the housing and actuate the activator using a single hand. Other configurations are also within the scope of the present disclosure, as discussed herein.

When received within the injector receiving region 26, the injector 16 may be described as being coupled to, connected to, supported by, or otherwise engaged with, injection assembly 12 in a defined orientation. Upon receiving a user input, for example, engagement, or actuation, of user actuation mechanism 22 by a user, such as a physician or medical technician, activator 20 is adapted to automatically and sequentially first, translate at least a portion of the injector 16 a predetermined translation distance 24 relative to the injection assembly 12 (e.g., to insert a portion of the injector, such as the needle of a syringe, into a patient's eye), and then second, dispense an injectant 18 from the injector (e.g., a volume of pharmaceutical into the vitreous chamber of the patient's eye), as schematically illustrated in FIG. 3. Accordingly, in practice, a physician or medical technician may position device 10 in an appropriate position adjacent a patient's eye. Because an associated injector 16 is coupled to the device, a portion of the injector, such as the needle of a syringe, is also positioned in an operative position adjacent the patient's eye. Additionally or alternatively, device 10 may be positioned in the appropriate position adjacent the patient's eye, and then the physician or medical technician may couple the injector to the device 10. Next, upon engagement of the user actuation mechanism 22, at least a portion of the injector, such as the needle of a syringe, will be inserted automatically into the patient's eye and a predetermined volume of injectant 18 will then be injected automatically into the eye. Illustrative, non-exclusive examples of user actuation mechanisms 22 include (but are not limited to) buttons, switches, and levers.

FIG. 4 schematically illustrates an illustrative, non-exclusive example of a device 10 together with an injector 16 in the form of a typical syringe. In FIG. 4, from left to right, the device is shown in a sequence of three configurations. As illustrated, injection assembly 12 may include a housing 32, a first piston, or translator, 34 adapted to engage the injector and translate it relative to housing 32, and a second piston, or translator, 36 adapted to engage a plunger 38 of the injector and translate it relative to housing 32 and relative to the body, or barrel, 40 of the injector. Accordingly, when injector 16 is coupled in an operative position with respect to device 10 and activator 20 is activated, first piston 34 automatically translates the injector 16 a predetermined translation distance 24 relative to the housing, and then second piston 36 automatically translates the plunger of the injector a predetermined plunging distance 42, relative to the housing. As a result, a predetermined volume of injectant is injected from the injector, for example via the dispensing conduit 39 coupled to the barrel 40 of the injector. First and second pistons 34, 36 may be described as being part of, or a component of, two-stage activator 20. First piston 34 and second piston 36 may additionally or alternatively be referred to as a barrel-translator 34 and a plunger-translator 36, respectively. Additionally or alternatively, although injector 16 is illustrated in FIG. 4 in the form of a typical syringe having a barrel 40, a plunger 38 slidingly received within the barrel, and a finger flange 44 extending from the barrel or as a portion of the barrel, it is within the scope of the present disclosure that devices 10 may be configured to receive and dispense an injectant from an injector that is configured differently than a typical, or conventional, syringe having the aforementioned components. In FIG. 4, the barrel-translator is schematically illustrated as being engaged with the finger flange of the syringe, but other configurations are also within the scope of the present disclosure, and FIG. 4 should be understood to schematically illustrate the relationship between the barrel-translator and the injector.

In FIG. 4, device 10 is illustrated in a sequence of configurations. Specifically, in the left depiction of intravitreal injection device 10, the device may be described as being in an injector-receipt configuration 41, in which the injector has been received by and secured to the injection assembly 12, and in which the injector has not yet been translated by the activator 20. Additionally or alternatively, the device may be described as being in a ready configuration 46 when device 10 is appropriately positioned adjacent to a patient's eye 3 and ready for actuation of the activator 20. More specifically, as discussed herein, the device may be in a ready configuration when an eye-contacting surface of alignment guide 14 is engaged with the surface of a patient's eye and an alignment portion of the alignment guide is aligned with a predetermined visible aspect of the patient's eye.

In the center depiction of intravitreal injection device 10 in FIG. 4, the device may be described as being in a translated configuration 43, in which injector 16 has been translated the translation distance 24. More specifically, in the translated configuration, at least the barrel-translator 34 has translated the injector the translation distance (relative to the injection assembly). When the device is being used and is appropriately positioned adjacent to a patient's eye, the dispensing conduit, or needle, of the injector will have been inserted into the patient's eye when the device is in the translated configuration, as illustrated in FIG. 4. In the translated configuration, plunger 38 has translated with the injector (relative to the injection assembly) but has not translated or otherwise moved relative to the injector. Device 10 may also be described as having a range of translation configurations, in which the injector is being translated by the activator from the injector-receipt configuration to the translated configuration, and which occur between the left and center depictions of the device in FIG. 4.

In the right depiction of intravitreal injection device 10 in FIG. 4, the device may be described as being in a dispensed, or plunged, configuration 45, in which the injectant has been dispensed from the injector by the activator. In the context of a device 10 being used with a typical syringe, plunger 38 of the injector has been translated the plunging distance 42 (relative to the injector) by the plunger-translator 36. Device 10 also may be described as having a range of plunging configurations, in which the injectant is being dispensed from the injector by the activator, and which occur between the center and right depictions of the device in FIG. 4. Additionally or alternatively, in the range of plunging configurations, the device may be described as translating the plunger-translator relative to housing 32.

Activator 20 may (although is not required to)—in addition to automatically translating injector 16 and then injecting an injectant therefrom—also automatically retract, or translate in an opposite direction, injector 16 a predetermined retraction distance relative to the injection assembly after the injectant has been dispensed. The retraction distance may or may not be equal to the predetermined translation distance 24; however, the retraction distance is at least great enough to completely remove the injector (e.g., the needle of a syringe) from the patient's eye. Accordingly, in some embodiments, activator 20 may be described as a three-stage activator. In such embodiments, a physician or medical technician may appropriately position device 10 adjacent a patient's eye, and upon actuation of the device (e.g., engagement of the user actuation mechanism), at least a portion of the injector will be inserted automatically into the patient's eye, a predetermined volume of injectant 18 will be injected automatically into the eye, and the injector will be automatically retracted, or removed, from the eye. Illustrative, non-exclusive examples of suitable durations for a procedure that comprises insertion of the injector, injection of a substance, and removal of the injector include (but are not limited to) time periods in the 2-4 second range. However, it is within the scope of the present disclosure that durations less than and/or greater than 2-4 seconds may be used.

Additionally or alternatively, devices 10 according to the present disclosure may be configured to automatically retract injector 16 in response to receiving an input from the user. For example, in some situations it may be desirable to abort or otherwise stop a procedure after the injector has been inserted in a patient's eye and prior to the injectant being dispensed, or at least fully dispensed, into the patient's eye. Additionally or alternatively, a device 10 may be configured to cease injection of the injectant prior to the injectant being fully injected into a patient's eye, such as in response to receiving an input from the user. Such inputs may be implemented in any suitable manner, including (but not limited to) an abort mechanism supported by the housing and adapted to receive a user input. Illustrative, non-exclusive examples of suitable abort mechanisms include (but are not limited to) buttons, switches, and levers. In some embodiments, the user actuation mechanism 22 may include the abort mechanism, and disengagement thereof, may cause the device to abort the procedure, whether it be to retract the injector or cease the dispensing of the injectant. Other configurations are also within the scope of the present disclosure.

In embodiments in which the activator is further adapted to automatically retract the injector the retraction distance, the activator may be described as including a biased retraction mechanism 49, as schematically indicated in FIG. 3. Additionally or alternatively, in some embodiments, the activator may be adapted to automatically retract the injector the retraction distance upon the user disengaging the user actuation mechanism. Other configurations are also within the scope of the present disclosure.

Additionally, although not required, intravitreal injection devices according to the present disclosure may have a range of retraction configurations, in which the injector is being retracted by the activator relative to housing 32. With reference to FIG. 4, the range of retraction configurations may somewhat correspond to the range of translation configurations, in so far as in the range of retraction configurations, the injector is translated out of the patient's eye from dispensed configuration 45 to a retracted configuration 47. However, it is within the scope of the present disclosure that in the optional range of retraction configurations, the plunger-translator 36 may or may not translate relative to the housing 20, and therefore the retracted configuration may or may not correspond to the injector-receipt configuration, as schematically indicated in FIG. 4.

Additionally, activator 20 and associated components of device 10 may be configured to operate smoothly and somewhat silently, if not completely silently, at least with respect to the hearing of a patient. Specifically, quiet or even silent operation of device 10 may facilitate an increased comfort level, or at least minimize disturbance, of the patient upon which the procedure is being performed and/or the physician or other medical technician performing the procedure. Similarly, smooth, non-jarring movement of the components of device 10 during use to position and inject a composition into a patient's eye also may provide these potential benefits.

Additionally or alternatively, devices 10 according to the present disclosure may be configured to control the rate at which a substance is injected into an eye. That is, an activator 20 may be configured to operate at a predetermined rate or rates (e.g., volume of injectant per unit time). Such predetermined rate(s) may vary depending on the particular configuration of injector being used, for example, depending on the size of needle of a syringe being used, and/or depending on the particular injectant being used. Additionally or alternatively, the rate may vary within a single operation of a device 10. For example, the rate may be linear. The rate may have an initial ramp up and then be linear or constant. The rate may be stepped. The rate may be parabolic or otherwise non-linear. Other rate profiles are also within the scope of the present disclosure. Additionally or alternatively, devices 10 may provide for adjustment of the rate at which an injectant is dispensed, for example, depending on a particular procedure being performed or condition being treated. Such adjustment may be automatic or may be user-defined. Illustrative, non-exclusive examples of suitable predetermined rates (based on total volume of injectant to be dispensed) of injection include (but are not limited to) rates equal to 10%/second, 20%/second, 30%/second, 40%/second, 50%/second, 60%/second, 70%/second, 80%/second, 90%/second, 100%/second, 10-50%/second, 30-70%/second, 50-90%/second, and 70-100%/second. It is within the scope of the present disclosure that predetermined rates that are less than, greater than, or within the illustrated rates and/or ranges of rates presented above, may be used without departing from the scope of the present disclosure.

Although illustrated in solid lines in FIG. 3 as being directly coupled to, or otherwise integral to, housing 32 of assembly 12, user actuation mechanism 22 may additionally or alternatively be remotely coupled to assembly 12 and two-stage activator 20, as schematically represented in dashed lines in FIG. 3. For example, in some embodiments it may be desirable to have a remote user actuation mechanism 22 to enable activation of the two-stage activator 20 without imparting a force onto housing 32, which could in turn jostle, or otherwise translate, the housing and the associated injector 16 relative to a patient's eye after the housing and injector have been appropriately positioned adjacent to the patient's eye. In such embodiments, the user actuation mechanism may be engaged by the same hand that is being used to position the housing adjacent to patient's eye, for example, in embodiments that include a stabilization device 28 that permits removal of the user's hand during a procedure, as discussed herein. Additionally or alternatively, the user actuation mechanism may be engaged by the user's other hand, for example, when the user retains a hand on the housing during use of the device.

Assembly 12 may, but is not required to be, adapted to receive and secure therein (and/or in a defined orientation and position relative therefor) various sizes and shapes of injectors, that is, injectors having different configurations. For example, assemblies 12 may be specifically adapted to receive and secure specific models of syringes, with such syringes varying in volume capacity, shape, size, etc. As illustrative, non-exclusive examples, the syringes having different configurations may include syringes having different volumes of barrels, having differently configured finger flanges, having differently configured plungers, and/or having differently configured or lengths of needles. Additionally or alternatively, assemblies 12 may be specifically adapted to receive and secure syringes of different manufacturers. Other configurations are also within the scope of the present disclosure. Accordingly, assemblies 12 according to the present disclosure may be adapted to be configured between one or more configurations, with each configuration adapted to receive and secure one or more configurations of injectors. For example, assembly 12 may include, or may be adapted to utilize, a plurality of inserts, such as pistons, or translators, 34, 36, that are specifically configured for use with specific injectors. For example, such inserts may include, or be configured to work in conjunction with, pistons 34, 36.

Additionally or alternatively, at least one of the barrel-translator 34 and the plunger-translator 36 may be selected from a plurality of translators configured to mate with a predetermined one or more of the syringes having different configurations. In such embodiments, the plurality of translators are adapted to be selectively received and released by the injection assembly 12 so that the intravitreal injection device can be configured by a user for use with a selected syringe from the syringes having different configurations.

Additionally or alternatively, assembly 12 may include adjustment mechanisms that are adapted to adjust, or configure, assembly 12 for receiving and securing various configurations of injectors, for example, by adjusting the size, shape, and/or configuration of injector receiving region 26. Other configurations are also within the scope of the present disclosure.

Additionally or alternatively, assemblies 12 may (but are not required to) be adapted to enable injections of various predetermined volumes of injectant 18, whether from a single configuration of an injector or syringe, or from various configurations of injectors or syringes. For example, assembly 12 may be adapted to utilize a plurality of inserts, such as one or both of pistons 34, 36, that are specifically configured for use with a specific injector to dispense a specific predetermined volume of a substance. Other configurations are also within the scope of the present disclosure.

Assemblies 12 according to the present disclosure may further include an illumination device, or light source, 48 supported by housing 32, as schematically illustrated in FIGS. 3-4. Such an illumination device may be provided and adapted to illuminate a patient's eye, such as the injection site thereon, during operation of device 10 and may take a variety of forms including, but not limited to, one or more light emitting diodes (LEDs).

As mentioned, devices 10 according to the present disclosure include an alignment guide 14. Alignment guides 14 according to the present disclosure are adapted to provide a mechanism by which a user, such as a physician or a medical technician, may appropriately position injector 16 adjacent and relative to a patient's eye. Accordingly, alignment guide 14 is supported relative to assembly 12, or housing 32 thereof, such that a predetermined portion of alignment guide 14 is a predetermined distance 52 from a predetermined portion of an associated injector 16, when present (or at least from a point in space where the predetermined portion of the injector will pass upon activation of device 10). For example, in some procedures, it may be desirable to insert the tip of the needle of a syringe, or other portion of an injector 16, into a patient's eye a predetermined distance away from a predetermined visible aspect of the eye (e.g., the iris or edge of the cornea) in order to avoid damaging various parts of the eye (e.g., the lens). Accordingly, during the procedure, the physician or medical technician may align the predetermined portion of the alignment guide with the predetermined visible aspect of the eye before activating the user actuation mechanism 22. Illustrative, non-exclusive examples of suitable predetermined distances 52 include (but are not limited to) distances equal to 2 mm, 3 mm, 4 mm, 5 mm, 6 mm, 1-4 mm, 1-8 mm, 2-8 mm, and 3-10 mm. It is within the scope of the present disclosure that predetermined distances 52 that are smaller than, larger than, or within the illustrated distances and/or ranges of distances presented above, may be used without departing from the scope of the present disclosure.

Stated differently, an alignment guide 14 may be supported relative to housing 32 and may include an eye-contacting surface 56 oriented to extend across a region of a surface of a patient's eye when a user positions an associated injector 16 adjacent to the patient's eye by appropriately manipulating housing 32 of assembly 12. The alignment guide may further include an alignment portion 55 that is adapted to be aligned with a predetermined visible aspect of the patient's eye when the eye-contacting surface is engaged with the surface of the patient's eye. The alignment portion is thus in a predetermined position (e.g., distance 52) relative to a predetermined injection site on the surface of the patient's eye, through which the dispensing conduit of the injector will pass when the injector is translated by activator 20.

Alignment guides 14 according to the present disclosure may be supported relative to housing 32 in a variety of configurations. For example, as schematically illustrated in solid lines in FIGS. 3-4, an alignment guide may be coupled directly or indirectly to injection assembly 12. In some such embodiments, the alignment guide may be removably and replaceably coupled to the assembly. Additionally or alternatively, a plurality of alignment guides having different configurations may be provided, for example, with each configuration being configured for use with a selected injector from a plurality of injectors having different configurations. Additionally or alternatively, as schematically illustrated in dash-dot and dash-dot-dot lines in FIGS. 3-4, an alignment guide may be, or may be adapted to be, coupled directly or indirectly to an associated injector 16. In some such embodiments, the alignment guide may be an integral portion of an injector. In other embodiments, the alignment guide may be adapted to be removably and replaceably coupled to an injector. Additionally or alternatively, the alignment guide may be adapted to be coupled to various configurations of injectors, such as to different configurations of syringes, as discussed herein. Additionally or alternatively, alignment guides according to the present disclosure may be adapted to be disposed of after one or more uses. For example, alignment guides may be pre-sterilized, for example by a manufacturer of alignment guides, and a physician or medical technician may use an alignment guide only once on a single patient and then dispose of the alignment guide.

In embodiments in which an alignment guide is coupled to, or is adapted to be coupled to, an injector, as optionally and schematically illustrated in FIGS. 3-4, at least a portion of the alignment guide is movable relative to the injector. This permits for translation of the injector by activator 20 of device 10 relative to a patient's eye, while eye-contacting surface 56 is engaged with the surface of the patient's eye. This relationship between the alignment guide and the injector is schematically illustrated in FIGS. 3-4 with an optional spring, or bias mechanism, 57. Additionally or alternatively, as also schematically illustrated in FIGS. 3-4, the alignment guide, or at least a portion thereof, may be in a sliding relation to the associated injector, as schematically indicated at 59. For example, with reference to the translated configuration 43 of device 10 in FIG. 4 (center depiction) and the dispensed configuration 45 of device 10 in FIG. 4 (right depiction), the bias mechanism 57 may be compressed and/or the alignment guide may slide, or translate, along, or relative to, the body 40 of the injector, when the injector is translated toward the patient's eye and the eye-contacting surface 56 is engaged with the surface of the patient's eye.

Devices 10 according to the present disclosure may include an optional switch 50, as schematically illustrated in FIGS. 3-4, or other mechanism that senses when a predetermined threshold contact force, or pressure, is applied against a patient's eye by the alignment guide. Switch 50 may additionally or alternatively be referred to as a pressure detector, a force detector, or simply a detector. Switch 50, when present, may be integral to, or otherwise coupled to, the alignment guide 14 and, for example, measure or detect the contact force, or pressure, applied against the eye by the alignment guide. Additionally or alternatively, such a switch 50 may be integral to, or otherwise coupled to, assembly 12 and, for example, to measure or detect relative force, or pressure, between the alignment guide 14 and the assembly 12 (e.g., the housing 32 thereof) due to pressure being applied against a patient's eye. Switch 50 may therefore be coupled to, or otherwise communicate with, activator 20 (as schematically illustrated in FIGS. 3-4) or user mechanism 22, such that activator 20 may not be actuated by a user, may not operatively translate an associated injector, and/or may not operatively dispense injectant from the injector unless a sufficient contact, or threshold, force, or pressure, is applied to the alignment guide, for example, by pressing the alignment guide against the surface of a patient's eye. Such a configuration may be desirable to prevent, or at least restrict, actuation of device 10 prior to device 10 being appropriately positioned adjacent and relative to a patient's eye. In some embodiments, switch 50 may be in electrical communication with the activator and/or the user actuation mechanism. Additionally or alternatively, in some embodiments, the detector may be in mechanical communication with the activator and/or the user actuation mechanism, for example, and configured to physically restrict or prevent actuation of one or both of the user actuation mechanism and the activator. Other mechanisms for restricting, or even preventing, actual injection prior to proper alignment and positioning of a device 10 adjacent and relative to a patient's eye are also within the scope of the present disclosure.

As schematically illustrated in FIGS. 3-4, devices 10 according to the present disclosure may include an optional notification mechanism 51 that is adapted to notify, or otherwise signal, a user of a device 10 of a predetermined criterion, for example, when a predetermined event has occurred. For example, notification mechanism 51 may signal a user when the force of the alignment guide against the surface of a patient's eye is at least a threshold force, when the force of the alignment guide against the surface of a patient's eye is not at least a threshold force, when the injector has been inserted to an appropriate depth in a patient's eye, when the injectant 18 has been fully injected (or at least when the device 10 has manipulated an injector to fully inject injectant 18), when the injector has been removed from the patient's eye, or when any other process or procedure of a device according to the present disclosure has occurred, been initiated, been completed, etc. Such a notification may be beneficial to notify a user when activation of device 10 is appropriate, when removal of device 10 away from a patient's eye is appropriate, etc. Notification mechanism 51 may include any suitable mechanism or device including visible indicator(s), such as one or more LEDs, and/or audible indicator(s), such as a buzzer or other sound-emitting mechanism.

A portion of an illustrative, non-exclusive example of an alignment guide 14 is schematically illustrated in FIGS. 5-6. FIG. 5 also schematically illustrates a dispensing conduit 39 of an injector 16, in both an initial position prior to being translated by device 10 and in a position in which the injector has been translated the translation distance 24. As illustrated, an alignment guide may include a foot, or base, 54 that includes an eye-contacting surface 56 and an alignment edge, or edges, 58. Edge(s) 58 also may be described as an alignment portion 55 or as defining an alignment portion 55 of an alignment guide 14. Foot 54 may additionally or alternatively be referred to as an eye-contacting portion of alignment guide 14.

Although in FIG. 5 the needle is illustrated as extending generally perpendicular to eye-contacting surface 56, it is also within the scope of the present disclosure that a device 10 may be configured such that a portion of an injector, such as a needle of a syringe, extends at a predetermined non-normal (non-perpendicular) angle relative to eye-contacting surface 56. For example, depending on the application, in some devices and/or methods, it may be desirable for the injector to penetrate the sclera at such a non-normal angle. For example, in embodiments of devices configured to inject a solid pellet into a patient's eye, the dispensing conduit of the injector may be larger than if a liquid or gaseous injectant were being used. In such situations, an angled incision path into the patient's eye may restrict the incision from leaking fluid, as an angled incision tends to be self-sealing due to the internal pressure of the eye. Additionally or alternatively, eye-contacting surface 56, while schematically illustrated as being planar, may be curved, or otherwise configured, to conform to the contoured surface of a typical human eye. Other configurations are also within the scope of the present disclosure.

As schematically illustrated in FIG. 6, edges 58 are spaced the predetermined distance 52 away from a point 61 through which the needle of an injector 16 may pass when a device 10 is actuated. The illustrative, non-exclusive example of a foot 54 that is schematically illustrated in FIGS. 5-6 may be described as U-shaped, and/or as having two prongs 60 extending from a leg 62. Such U- or V-shaped feet may permit unobstructed viewing of an injection site on a patient's eye during a procedure using device 10. Other configurations are equally within the scope of the present disclosure, including feet 54 having a single prong, or projection, extending from a leg.

Additionally or alternatively, while prong(s) 60 are schematically illustrated as perpendicularly extending from leg 62, it is also within the scope of the present disclosure that prong(s) 60 may extend from leg 62 at a non-normal angle. Such a configuration may facilitate insertion of an injector 16 at a non-normal angle relative to the surface of a patient's eye.

Although not required, feet, or other eye-contacting portions, 54 according to the present disclosure may include one or more gripping regions 64 that provide increased friction, or other increased gripping, between eye-contacting surface 56 and a patient's eye to aid in the positioning and securing of the eye-contacting portion 54 against the surface of a patient's eye. For example, such regions 64 are schematically illustrated in FIG. 5 as protrusions, or teeth, that extend from the eye-contacting surface 56. Gripping regions 64 according to the present disclosure may take various forms, including various shapes and sizes, such that gripping regions 64 generally grip the surface of a patient's eye and thereby generally restrict lateral movement of the eye-contacting portion 54 of the alignment guide 14 relative to the surface of the eye once the eye-contacting portion 54 has been appropriately positioned by a physician or medical technician. Additional illustrative, non-exclusive examples of gripping regions according to the present disclosure may include suctioning structure, such as (but not limited to) suction cups and/or openings operatively coupled to a vacuum mechanism, as discussed herein.

As schematically illustrated in FIGS. 5-6, eye-contacting portions 54 according to the present disclosure may further include (but are not required to include) an eyelid engagement shoulder, or flange, 66 generally opposite of the prong(s) 60 relative to leg 62. Shoulder 66 may additionally or alternatively be described as an eyelid engagement flange. Other configurations and locations of a shoulder 66 are also within the scope of the present disclosure. Shoulder 66, when present, restricts a patient's eyelid from interfering with the procedure and operation of device 10 in that it is adapted to engage and restrict the eyelid from closing on, or over, a portion of the eye-contacting portion 54 that would interfere with the operation of device 10 or with a physician's or medical technician's ability to see the necessary portion of the eye for positioning device 10. Stated differently, an eyelid engagement flange may be provided to restrict a patient's eyelid from covering the injection site on the patient's eye, to restrict the patient's eyelid from obstructing the user's sight of a predetermined visible aspect of the patient's eye (e.g., the edge of the iris or cornea), and/or to restrict the patient's eyelid from obstructing the user's sight of alignment portion 55.

As mentioned, alignment guides 14 according to the present disclosure, or at least a portion thereof, may be selectively coupled to assembly 12. For example, depending on the configuration of a device 10 according to the present disclosure, attachment of an associated injector 16 may be at least partially facilitated by removal of, omission of, or translation of, an alignment guide, for example, to appropriately position the injector within the injector receiving region 26 of assembly 12. Additionally or alternatively, alignment guides 14 and/or a portion thereof, such as eye-contacting portion 54, may be configured for limited use, such as a single use. In such embodiments, the alignment guide or eye-contacting portion thereof may be pre-sterilized and adapted to be attached to assembly 12 only for a single instance of a use of a device 10. As such, a new, sterile alignment guide, or portion thereof, may be used for each patient, with each alignment guide, or portion thereof, being used only once to thereby avoid contamination of a subsequent patient's eye.

Additionally or alternatively, removable portions of alignment guides may allow for a plurality of configurations of eye-contacting portions 54 to be used with a single device 10. For example, eye-contacting portions with differing predetermined distances 52 may be provided, such as to permit use of a single device 10 with patients having different size eyes, or for different procedures requiring different locations of injections, etc.

Additionally or alternatively and as schematically illustrated in FIG. 6, eye-contacting portion 54 according to the present disclosure may include indicia, or a marking or markings, 70 that enable a physician or medical technician to align the alignment guide relative to a visible aspect of a patient's eye, other than or in addition to using edge(s) 58. Markings 70 may include a plurality of markings, such as on a scale of known increments (e.g., millimeters). Such a scale may extend from or be based on distances from edge(s) 58, or additionally or alternatively may extend from or be based on distances from the point 61 through which a portion of the injector 16 extends upon actuation of a device 10, as schematically illustrated in FIG. 6. Accordingly, a single alignment guide 14, or eye-contacting portion 54 thereof, may be used with patients with various eye sizes or for different procedures requiring varying predetermined distances 52.

FIG. 7 schematically illustrates another example of an eye-contacting portion 54 according to the present disclosure. The eye-contacting portion 54 illustrated in FIG. 7, rather than including a pair of prongs, includes an opening, hole, or passage, 68, through which a portion of an associated injector (e.g., the needle of a syringe) may extend. The passage may be described as having an enclosed inner perimeter. An eye-contacting portion 54, such as that illustrated in FIG. 7, may be described as a closed eye-contacting portion, while an eye-contacting portion 54 such as that illustrated in FIG. 6 may be described as an open eye-contacting portion. The eye-contacting portion 54 of FIG. 7 includes an alignment edge 58 that is spaced the predetermined distance 52 away from the point 61 through which the portion of the injector will extend upon actuation of a device 10 according to the present disclosure. As schematically illustrated in FIG. 7, edge 58 optionally may be curved, or contoured, such as to generally conform to the circular shape of a patient's iris, or other portion of the patient's eye. Such a configuration, although not required, may be beneficial when aligning the eye-contacting portion 54 adjacent and relative to a patient's eye, for example, both in position and angle relative to the edge of a patient's iris. Similarly, though not illustrated in FIG. 6, eye-contacting portions 54 with one or more prongs 60 may also include curved alignment edges 58.

Another illustrative, non-exclusive example of an eye-contacting portion 54 according to the present disclosure is schematically illustrated in FIG. 8. The eye-contacting portion 54 of FIG. 8, similar to the eye-contacting portion of FIGS. 5-6, includes a pair of prongs 60 extending from a leg 62. However, rather than having a pair of alignment edges 58 corresponding to the ends of the prongs distal to leg 62, eye-contacting portion 54 of FIG. 8 includes a single curved alignment edge 58 corresponding to a longitudinal edge of only one of the pair of prongs 60. This alignment edge is curved to generally conform to the circular shape of a patient's iris. Additionally or alternatively, as schematically illustrated in FIG. 8, the other prong 60 may act as an eyelid engagement shoulder, or flange, 66.

Some embodiments of alignment guides 14 according to the present disclosure may be constructed, or at least partially constructed, of a transparent, or at least translucent, material to permit easier visibility of a patient's eye during operation of a device 10 according to the present disclosure. In some such embodiments, the alignment guide also may be illuminated, for example, by optional illumination device 48. In such embodiments, the illumination device may be well suited for illuminating the alignment guide without shining light directly in the patient's eye, or pupil thereof. Other configurations are also within the scope of the present disclosure.

Another illustrative, non-exclusive example of an alignment guide 14 according to the present disclosure is illustrated in FIG. 9 and is indicated generally at 200. Alignment guide 200 includes a body 202 that is constructed of a transparent, or at least translucent, material. Body 202 includes a passage 204 that is configured to permit a portion of an injector 16, such as a dispensing conduit 39 or needle of a syringe, to translate therethrough. Body 202 defines an internal volume 206 and includes an eye-contacting surface 56, a portion of a perimeter of which is defined by a curved alignment edge 58. One or more holes, or ports, 208 extend through the eye-contacting surface 56 of guide 200, and at least one hole, or port, 210 extends through an opposite side of guide 200, as illustrated in FIG. 9. Guide 200 may additionally include coupling structure 212 adapted to couple, or otherwise mate, or connect, the alignment guide to an assembly 12 according to the present disclosure. Accordingly, guide 200 may be used with a device 10 that incorporates a vacuum, or suction, mechanism 214 (as schematically indicated in FIG. 3) operatively coupled to hole 210. In such an embodiment, eye-contacting surface 56 may be placed against a patient's eye, and the associated vacuum mechanism may provide a suction action on the patient's eye, thereby securing the alignment guide thereto and restricting lateral movement relative to the patient's eye upon appropriate placement thereon. Such an embodiment also may be illuminated to enable a physician's or medical technician's viewing of the patient's eye during the procedure.

Turning now to FIGS. 10-12, another illustrative, non-exclusive example of an alignment guide 14 according to the present disclosure is illustrated and is indicated generally at 400 together with an associated injector 16 in the form of a syringe and a patient's eye 3. Alignment guide 400 includes a resiliently flexible band 402 extending from a leg, or support, 62. The flexible band includes eye-contacting surface 56 and an edge 58 that defines an alignment portion 55 of the alignment guide. As seen in the sequence of FIGS. 10-12, the flexible band is adapted to at least partially conform to the surface of the patient's eye when the alignment guide is positioned against the patient's eye, for example, when the injection assembly of the intravitreal injection device is translated toward the patient's eye by the user of the device, as schematically indicated by the arrows in FIGS. 10-12. With reference to FIGS. 10-12, the flexible band may flex from a neutral, unflexed, configuration 404 (FIG. 10), to an intermediate, or partially, flexed configuration 406 (FIG. 11), and then to a fully flexed configuration 408 (FIG. 12). When the alignment guide is translated away from the patient's eye, the resiliently flexible band may return (such as responsive to its own bias) to the unflexed configuration.

In some embodiments of alignment guides 400, although not required, the resiliently flexible band 402 may be adapted to restrict translation of the injection assembly toward the patient's eye after a predetermined operating distance away from the patient's eye. In other words, the flexible band may have a built-in stop, or other internal bias, or structure, that restricts, or even prevents, the flexible band from flexing beyond a certain point. That is, the alignment guide may prevent further flex of the resiliently flexible band 402 beyond the fully flexed configuration 408. Such a configuration may be constructed in any suitable manner. For example, the alignment guide may include a spring or other biasing structure that bottoms out, or prevents translation upon a predetermined amount of compression of the structure. The flexible band may additionally or alternatively have portions of varying flexibility, including one or more portions with nearly zero flexibility. For example, with reference to the resiliently flexible band illustrated in FIGS. 10-12, the region of the band distal the leg 62 may be more flexible than the region of the band proximate to the leg. The material or materials from which the flexible band is constructed may also determine the degree of flexibility of the band and portions thereof. Other configurations are also within the scope of the present disclosure.

Additionally or alternatively, the resiliently flexible band may be adapted to exert an opposing force (that is, opposed to a force applied by a user translating the injection assembly toward the patient's eye) that biases the injection assembly away from the patient's eye and to restrict, or even prevent, translation of the injection assembly toward the patient's eye beyond a predetermined operating distance away from the patient's eye. Additionally or alternatively, the resiliently flexible band may be adapted to dampen translation of the injection assembly relative to the patient's eye. Other configurations are also within the scope of the present disclosure.

Additionally or alternatively, as illustrated in dash-dot-dot lines in FIG. 10, the resiliently flexible band may extend on more than one side of the injector, or at least the dispensing conduit thereof. For example, leg 62 may extend at least partially around the injector and/or more than one leg may be provided, from which the resiliently flexible band extends. In some such embodiments, the resiliently flexible band may include, or define, a passage through which the dispensing conduit translates when the injector is translated by the activator.

FIGS. 13-15 illustrate another illustrative, non-exclusive example of an alignment guide 14 according to the present disclosure, which is indicated generally at 500 and is shown together with an associated injector 16 in the form of a syringe and a patient's eye 3. Alignment guide 500, similar to alignment guide 400 of FIGS. 10-12, includes a resiliently flexible band 502; however, the flexible band of alignment guide 500 is adapted to be coupled to the injector 16 and includes, or defines, a passage 504, through which the dispensing conduit of the injector passes when the injector is translated toward the patient's eye and the flexible band is caused to flex, or compress. Additionally or alternatively, alignment guide 500 may be integral to an injector. For example, an injector may be manufactured with, or assembled with, a presterilized alignment guide 500 together with a cap, or covering, that a user removes prior to engaging the alignment guide with the surface of a patient's eye. Other configurations are also within the scope of the present disclosure.

Alignment guide 500 may or may not be used with an intravitreal injection device according to the present disclosure, and may simply be used together with an injector. In some such embodiments, the injector may be configured so that use of the injector in combination with the alignment guide may be performed simply by grasping the plunger of the injector, positioning the alignment guide against the surface of a patient's eye, and translating the plunger toward the patient's eye. This translation of the plunger may first compress the flexible band, and then when the alignment guide is in its fully flexed configuration, the friction between plunger and the barrel of the injector is overcome and the injectant is dispensed from the injector. Other configurations are also within the scope of the present disclosure.

Flexible band 502 includes eye-contacting surface 56 and an edge 58 that defines an alignment portion 55 of the alignment guide, and like alignment guide 400 and as seen in the sequence of FIGS. 13-15, alignment guide 500 may be configured from an unflexed configuration 404 (FIG. 13), to an intermediate flexed configuration 406 (FIG. 14), to a fully flexed configuration 408 (FIG. 15). The other characteristics of flexible band 402, discussed herein, may additionally or alternatively be incorporated into flexible band 502 of alignment guide 500.

Referring back to FIG. 3, and as mentioned, some injection devices 10 according to the present disclosure may further include (but are not required to include) a stabilization device, or assembly, 28 that couples, or at least selectively couples, the injection assembly 12 to a foundation, or base, 30. The stabilization assembly may therefore be adapted to facilitate a user's manipulation of the injection assembly's housing 32 to position an injector adjacent to a patient's eye. Accordingly, stabilization device 28 may enable a user to position assembly 12 in an appropriate position adjacent a patient's eye, and then remove his/her hand or hands therefrom in order to avoid inadvertent movement of the assembly during a procedure. Stated differently, the stabilization assembly may be adapted to retain the housing in a selected position when a user selectively releases the housing. Additionally or alternatively, stabilization assembly 28 may provide a counterbalancing mechanism for the activator assembly 12. That is, stabilization assembly 28 may permit precise positioning of the activator assembly 12 and permit a user to remove his/her hands therefrom without the activator assembly subsequently moving due to its own weight. Additionally or alternatively, stabilization assembly 28 may provide a damping mechanism against tremor, for example, so that a physician or medical technician may precisely position a device 10 and not worry about it springing back, bouncing, or otherwise generally moving from the position in which it is placed. Additionally or alternatively, such a mechanism may aid in restricting a patient from moving his/her eye while in contact with the alignment guide 14 because the stabilization assembly prevents movement of the device without sufficient force greater than would likely result from a patient attempting to move or accidentally moving his/her eye or head.

Stabilization assembly 28 may include a mechanical arm that includes hydraulic elements, spring elements, damping elements, and/or other elements that aid in the positioning and stabilization of assemblies 12 according to the present disclosure. Base 30 may include a portable base, such as may be used to transport a device 10 from one patient to another, from one patient operating/examination room to another, around a patient operating/examination table or chair, etc. Additionally or alternatively, base 30 may include a floor or wall or other stationary foundation to which stabilization assembly 28 may be securely coupled. Additionally or alternatively, base 30 may include a patient operating/examination table or chair. Other configurations are also within the scope of the present disclosure.

Illustrative, non-exclusive examples of portions of intravitreal injection devices 10 according to the present disclosure are somewhat less schematically illustrated in FIGS. 16-21. Where appropriate, the reference numerals from the schematic illustrations of FIGS. 3-15 are used to designate corresponding parts of injection devices 10 according to the present disclosure; however, the examples of FIGS. 16-21 are non-exclusive and do not limit the present disclosure to the illustrated embodiments. That is, neither injection devices nor various component parts thereof are limited to the specific embodiments disclosed and illustrated in FIGS. 16-21, and injection devices 10 according to the present disclosure may incorporate any number of the various aspects, configurations, characteristics, properties, etc. illustrated in the embodiments of FIG. 16-21, of FIGS. 3-15, as well as variations thereof and without requiring the inclusion of all such aspects, configurations, characteristics, properties, etc. For the purpose of brevity, each previously discussed component part, or variant thereof, may not be discussed again with respect to FIGS. 16-21; however, it is within the scope of the present disclosure that the previously discussed features, variants, etc. may be utilized with the illustrated embodiments of FIGS. 16-21. Similarly, it is also within the scope of the present disclosure that all of the component parts, and portions thereof, that are illustrated in FIGS. 16-21 are not required to all embodiments according to the present disclosure. The various component parts illustrated in FIGS. 16-21 are not illustrated to scale.

Turning first to FIG. 16, a portion of an illustrative, non-exclusive example of an intravitreal injection device 10 according to the present disclosure is illustrated and indicated generally at 100. Device 100 includes an alignment guide 14 having an open eye-contacting portion 54 that includes an eyelid engagement shoulder 66. Although not illustrated in this example, the eye-contacting portion 54 of device 100 may additionally include such features as markings 70 and/or a switch 50, which may be integral thereto or otherwise operably coupled thereto.

Device 100 further includes an injection assembly 12 that includes an injector receiving region 26. The illustrated assembly 12 of device 100 further includes a retaining member 102 hingedly coupled to housing 32 of assembly 12, and which selectively retains a syringe 16 within the receiving region 26 so that the needle of the syringe is appropriately positioned relative to the eye-contacting portion 54. Accordingly, a syringe may be selectively inserted into and removed from device 100. Retaining member 102 is illustrated as having a clip, or snap-fit, arrangement with housing 32. Other configurations are also within the scope of the present disclosure.

Assembly 12 of device 100 includes a barrel-translator 34 and a plunger-translator 36 in a coaxial arrangement with each other and with housing 32, although other configurations are also within the scope of the present disclosure. Barrel-translator 34 of device 100 is adapted to receive and engage a finger flange 104 of the syringe. Accordingly, when the barrel-translator translates within housing 32, the entirety of the syringe will translate with it, including plunger 38, assuming plunger 38 has a sufficient friction fit arrangement with the body 40 of the syringe and/or assuming the plunger-translator is simultaneously translating the plunger, depending on the configuration of activator 20 embodied in the device 10. When plunger-translator 36 translates relative to the barrel-translator, the plunger 38 will be forced to translate relative to the body 40 of the syringe, and thereby inject an injectant contained within the syringe.

As illustrated in cross-section in FIG. 16, barrel-translator 34 and plunger-translator 36 of device 100 include tongues 106, 108, respectively, that slide within corresponding grooves 110, 112, of housing 32 and the barrel-translator, respectively. Accordingly, translators 34, 36 are restricted from rotating within housing 32 as well as relative to each other. The tongues and grooves may be keyed or otherwise configured to permit insertion in housing 32 only in a specific orientation. Other configurations are also within the scope of the present disclosure that provide a restriction against relative rotation of the pistons. For example, the tongues and grooves may be reversed from the configuration illustrated. Additionally or alternatively, the translators may be shaped without tongue and grooves to permit relative longitudinal movement while restricting relative rotational movement (e.g., with a non-circular cross-section). Configurations in which the translators are permitted to rotate relative to each other are also within the scope of the present disclosure.

In embodiments of device 100 that are configured to permit utilization of various sizes and shapes of injectors and/or extractors, the translators may be specifically designed for a specific configuration of injector and/or extractor. For example, the lengths and diameters of the translators may vary corresponding to a particular syringe, or other injector or extractor, being used. Housing 32 may therefore be configured to permit the removal and replacement of translators 34, 36, such that a physician or medical technician may install an appropriate configuration of translators for a particular configuration of syringe, or other injector or extractor, being used.

As illustrated with dashed lines and reference numerals 48, 50, injection devices 100 according to the present disclosure may additionally include such features as an illumination device 48 for lighting the alignment guide and patient's eye and/or a switch 50 for detecting a predetermined threshold force, or pressure, against the surface of a patient's eye by the alignment guide 14.

FIGS. 17-21 somewhat schematically illustrate illustrative, non-exclusive examples of portions of activators 20 according to the present disclosure that may be incorporated into intravitreal injection device 100 or into any other intravitreal injection device 10 according to the present disclosure. With respect to device 100 of FIG. 16, the activator portions of FIGS. 17-21 may be supported by, or positioned within, housing 32 generally to the right of the cross-section (i.e., away from the needle 39) illustrated in FIG. 16. Other configurations are also within the scope of the present disclosure, and as discussed, the optional embodiments of FIGS. 17-21 are not limited to being incorporated into device 100 of FIG. 16, and devices 10 according to the present disclosure are not limited to including one of the optional activators 20 illustrated in FIGS. 17-21.

A portion of an illustrative, non-exclusive example of an activator 20 according to the present disclosure is illustrated in FIG. 17 and indicated generally at 600. Activator 600 may be described as including a cam system. To facilitate longitudinal translation of barrel-translator 34 and plunger-translator 36, activator 600 includes a first cam 120 coupled to a second cam 122. First cam 120 and second cam 122 may additionally or alternatively be referred to as plunger-cam 120 and a barrel-cam 122, respectively. First cam 120 is configured to engage and translate at least the plunger-translator, and second cam 122 is configured to engage and translate at least the plunger-translator. Accordingly, as the cams rotate (counter-clockwise as illustrated in FIG. 17), an associated injector will first be translated the translation distance, and then the plunger of the injector will be translated the plunger-distance. In some examples, first cam 120 may (but is not required to) engage both translators 34, 36 to ensure that upon initial translation of first piston 34, it is not translated relative to second piston 36; however, if there is sufficient internal friction between the plunger of the syringe and the body of the syringe, such an arrangement may not be necessary. Additionally or alternatively, the first and second cams may be referred to as portions, or components, of the plunger-translator and the barrel-translator, respectively. Rotation of the cams may be accomplished by any suitable mechanism. As an illustrative, non-exclusive example, a first gear 126 may be coupled to the cams and be engaged with a second gear 128, which in turn may be coupled to a motor, such as a step motor, 124. Additionally or alternatively, a lever arm may be directly or indirectly coupled to the cams, such that rotation of the lever by a user causes the cams to rotate, and thus the translators to translate the injector and the plunger thereof.

In embodiments of device 10 that are configured to permit utilization of various sizes and shapes of injectors and/or extractors, first and second cams 120, 122 may be specifically designed for a specific configuration of injector and/or extractor. For example, the shape and size of the cam lobes may vary corresponding to a particular syringe, or other injector or extractor, being used. The injection assembly 12, or housing 32 thereof, may therefore be configured to permit the removal and replacement of the first and second cams, such that a physician or medical technician may install an appropriate configuration of cams for a particular configuration of syringe, or other injector or extractor, being used.

FIGS. 18-19 illustrate a portion of another illustrative, non-exclusive example of an activator 20 according to the present disclosure, and which is indicated generally at 700. Activator 700 may be described as including a concentric screw system, and includes an internally threaded casing 702 that is adapted to rotate in response to a user engaging a user actuation mechanism of an intravitreal injection device according to the present disclosure. Barrel translator 34 and plunger translator 36 of activator 700 may be described as, or may include, an externally threaded barrel-driver 704 and an externally threaded plunger-driver 706, respectively, both (at least initially) in threaded engagement with casing 702, as illustrated in FIG. 18. The threads of the casing extend for a predetermined length, such that when the casing rotates relative to housing 32 in a first rotational direction a first predetermined number of rotations, the barrel-driver and the plunger-driver translate an associated injector, and when the casing rotates in the first rotational direction a second predetermined number of rotations, beyond the first predetermined number of rotations, the plunger-driver translates the plunger of the injector relative to the barrel of the injector. This relationship between the barrel-driver, the plunger-driver, and the casing is seen in the sequence of FIGS. 18-19. In FIG. 18, which illustrates the activator in what may be described as injector-receipt configuration 41 of the device, both the barrel-driver and the plunger-driver are in threaded engagement with the casing. However, as the casing rotates, the barrel-driver is translated beyond the extent of the internal threads of the casing, as illustrated in FIG. 19, while the plunger-driver remains in threaded engagement with the casing and therefore continues to translate. In FIGS. 18-19, the casing is illustrated as being coupled to a motor 708; however, other configurations are also within the scope of the present disclosure, including embodiments in which the casing is rotated in response to a user engaging a lever arm, or other non-electrical assembly.

FIG. 20 illustrates a portion of yet another illustrative, non-exclusive example of an activator 20 according to the present disclosure, and which is indicated generally at 800. Activator 800 may be described as including a linkage system including a plurality of links. For example, the barrel-translator 34 may be described as, or may include, a barrel-link 802, and the plunger-translator 36 may be described as, or may include, a plunger-link 804. As illustrated in FIG. 20, the barrel-link is hingedly coupled to housing 32 via a series of links 806, 808, which are directly or indirectly coupled to, or engaged by, a user actuation mechanism of the device. Accordingly, as indicated by the arrow 810, when a force is applied to one or both of, or the intersection between the two, links 806, 808, for example, via a user actuation mechanism, the barrel-link will translate, which in turn will translate an associated injector.

Plunger-link 804 is hingedly coupled to barrel-link 802, as illustrated in FIG. 20, via a series of links 812, 814, which are positioned somewhat adjacent to links 806, 808. Accordingly, when links 806, 808, or the intersection between the two, engage (either directly or indirectly) one of links 812, 814, or the intersection between the two, in response to user engagement of the user actuation mechanism, the plunger-link will translate, which in turn will translate the plunger of the associated injector. Accordingly, depending on the specific geometry of the linkage system of activator 800, in response to user engagement of the user actuation mechanism, the barrel-translator will first translate the syringe a distance, and then the plunger-translator will translate the plunger a distance. In some embodiments, the barrel-translator continues to translate the barrel of the injector while the plunger-translator translated the plunger relative to the barrel; however, it is within the scope of the present disclosure that an activator 800 may be configured so that the barrel-translator translates the syringe the translation distance prior to the plunger-translator translating the plunger the plunger-distance.

FIG. 21 illustrates a portion of yet another illustrative, non-exclusive example of an activator 20 according to the present disclosure, and which is indicated generally at 900. Activator 900 may be described as including a rack and pinion system. Barrel-translator 34 includes a barrel-pinion 902 and a barrel-rack 904, and plunger-translator 36 includes a plunger-pinion 906 and a plunger-rack 908. As illustrated in FIG. 21, the barrel-pinion is adapted to engage the barrel-rack for only a portion of its rotational movement. For example, the barrel-pinion may be truncated (as illustrated in FIG. 21) and/or the gears associated with the barrel-pinion may extend for only a portion of the perimeter of the barrel-pinion, so that when the barrel-pinion rotates (in a clockwise direction illustrated in FIG. 21), the barrel-rack will translate the translation distance and stop, even if the barrel-pinion continues to rotate. The plunger-pinion, which is coupled to the barrel-pinion, is adapted to remain engaged with and to continue to translate the plunger-rack when the barrel-pinion ceases to translate the barrel-rack.

As optionally illustrated in FIG. 21, an input lever 910 may be coupled to the barrel-pinion and the plunger-pinion so that they all rotate together. Accordingly, when a user causes the input lever to pivot, for example, via engagement of the user actuation mechanism, a first predetermined angle, the barrel-rack and the plunger-rack translate the injector the translation distance, and when the input lever is pivoted a second predetermined angle beyond the first predetermined angle, the plunger-rack translates the plunger of the injector relative to the barrel of the injector. Activator 900 may additionally or alternatively include a motor that selectively rotates the barrel-pinion and the plunger-pinion in response to user engagement of the user actuation mechanism. Other configurations are also within the scope of the present disclosure.

As discussed, the activators 20 illustrated in FIGS. 16-21 are illustrative, and non-exclusive. Activators according to the present disclosure may be electrically powered. Alternatively, activators according to the present disclosure may not be electrically powered. Additionally or alternatively, an activator may be at least partially pneumatically controlled. Additionally or alternatively, an activator may be at least partially hydraulically controlled. Other configurations are also within the scope of the present disclosure.

Turning now to FIG. 22, illustrative, non-exclusive examples of methods according to the present disclosure are illustrated and indicated generally at 300. Methods according to the present disclosure may be performed by a user of an intravitreal injection device 10 (such as indicated generally at 302), by an intravitreal injection device 10 itself (such as indicated generally at 304), and/or by a combination of the two (such as indicated generally at 306). FIG. 22 schematically illustrates the general relationship between steps performed by a user and steps performed by an injection device, but such indications are not limiting in that such corresponding steps are not necessarily performed at an identical moment in time, and the relationships are depicted for illustrative purposes only. FIG. 22 illustrates some steps in dashed boxes, with such dashed boxes indicating that such steps are optional, and performance thereof may be dependent on whether a particular embodiment of an intravitreal injection device 10 is being used and/or on whether a physician or medical technician chooses to perform such steps. The methods and steps illustrated in FIG. 22 are not limiting and other methods and steps are also within the scope of the present disclosure, including methods having greater than or fewer than the number of steps illustrated, as should be understood from the description of intravitreal injection devices 10 according to the present disclosure and the various optional and alternative components and embodiments thereof. Finally, although not indicated in FIG. 22 with reference numerals, the discussion below of methods 300 according to the present disclosure makes reference to the various components of injection devices 10 according to the present disclosure and their associated reference numerals used herein.

As indicated at 310, a user may first secure an injector 16, such as a syringe, or other injector or extractor, to the injection device 10. However, as illustrated in dashed lines, the user may first be required to fill the injector with a substance, or injectant, as indicated at 312, if a pre-filled injector is not being used.

Additionally, as indicated in dashed lines at 314, the user may optionally need to attach an alignment guide, such as a sterile alignment guide, to the injection assembly of the injection device, if such a configuration of an injection device is being used. Alternatively, as also illustrated in dashed lines, attachment of an alignment guide may be performed after the injector is secured to the injection device, depending on the configuration of the injection device being used and/or depending on a preference by the user.

Next, as indicated generally at 316, the user may position the eye-contacting portion 54 of the injection device 10 in an appropriate position adjacent and relative to the patient's eye, for example, using the edge(s) 58 of the eye-contacting portion 54. Coinciding with step 316, and when an injection device is being used that incorporates a switch 50 for detecting a predetermined threshold force, or pressure, against a patient's eye, such an injection device determines whether or not the threshold pressure is achieved (e.g., by switch 50), as indicated generally in dashed lines at 318. If the threshold pressure is not achieved when using such an injection device, then the injection device may restrict actuation of the injection of the injectant, as discussed herein. If the threshold pressure is achieved when using such an injection device, then the injection device may permit actuation of the injection of the injectant. Additionally or alternatively, a notification mechanism 51 may notify the user whether or not the threshold pressure is achieved.

Next, as indicated generally at 320, the user may actuate the injection device, for example, by engaging user actuation mechanism 22. When the injection device is actuated, the injection device will translate the injector the predetermined translation distance 24 so that the dispensing conduit, or needle, of the injector will be inserted into the patient's eye an appropriate depth, as indicated generally at 322. Next, the injection device will translate the plunger of the injector a predetermined plunging distance 42 so that the injectant is injected into the patient's eye, as indicated generally at 324.

In some methods (e.g., in methods that utilize an injection device 10 having a two-stage activator 20 that is not additionally configured to retract the syringe), a user may then remove the needle from the patient's eye by manually retracting the device from its position adjacent the patient's eye, as indicated generally in dashed lines at 326. On the other hand, in methods that utilize an injection device 10 that incorporates a three-stage activator 20, the injection device 10 may automatically translate, or retract, the syringe so that the needle is automatically removed from the patient's eye, as indicated generally in dashed lines at 328.

Upon retraction of the needle from the patient's eye, whether by the user of the injection device or by the injection device itself, the injector may be removed from the injection device, as indicated generally in dashed lines at 330. Also, the injector and alignment guide may be disposed of, as indicated generally in dashed boxes at 332 and 334, respectively. Although steps 330, 332, and 334 are illustrated sequentially in FIG. 22, it is within the scope of the present disclosure that the alignment guide may be disposed of prior to removal of the injector from the injection device (330) and/or prior to disposal of the injector (332).

The discussion of devices 10 and methods according to the present disclosure primarily have been in the context of injecting a substance into the vitreous chamber of a patient's eye; however, also within the scope of the present disclosure are devices configured to, or used to, inject or extract a substance to and/or from any other suitable portion of a patient's body. Accordingly, the devices 10 and methods 300 according to the present disclosure may be used for and/or modified to be used for injecting and/or extracting a substance to and/or from portions of a patient's body other than the eye. Therefore, the use of "patient's eye," "eye-contacting surface," and similar terms or phrases used herein should be interpreted to also include "patient's body" (such as, but not limited to, various soft and/or delicate tissues of a patient's body), "body-contacting surface," etc. As an illustrative, non-exclusive example, devices and methods according to the present disclosure may be utilized to inject and/or extract a substance from a portion of a patient's inner ear. Other body portions are also within the scope of the present disclosure. Stated differently, devices and methods according to the present disclosure are not limited to be implemented within the field of opthalmology.

The following enumerated paragraphs represent illustrative, non-exclusive ways of describing inventions according to the present disclosure.

A1 An intravitreal injection device, comprising:
 an injection assembly adapted to selectively receive an injector containing an injectant and having a dispensing conduit and secure the injector to the injection assembly in a defined orientation, wherein the injection assembly is further adapted to selectively release the injector from the injection assembly, and wherein the injection assembly comprises:
  a housing adapted to be selectively grasped by a user and manipulated to position the injector adjacent to a patient's eye when the injector is secured to the injection assembly;
  a user actuation mechanism supported by the housing and adapted to be engaged by the user; and
  an activator supported by the housing, wherein responsive to the user engaging the user actuation mechanism, the activator is adapted to automatically and sequentially first, translate the injector a translation distance relative to the injection assembly and then second, dispense the injectant from the injector; and
 an alignment guide supported relative to the housing (e.g., coupled to the injection assembly or adapted to be coupled to the injector), wherein the alignment guide includes an eye-contacting surface oriented to extend across a region of a surface of the patient's eye when the user positions the injector adjacent to the patient's eye, and an alignment portion adapted to be aligned with a predetermined visible aspect of the patient's eye when the eye-contacting surface is engaged with the surface of the patient's eye, wherein the alignment portion is in a predetermined position relative to a predetermined injection site on the surface of the patient's eye through which the dispensing conduit of the injector will pass when the injector is received by and secured to the injection assembly and translated by the activator.

A2 The intravitreal injection device of paragraph A1, wherein the dispensing conduit includes at least one needle through which the injectant is selectively dispensed.

A3 The intravitreal injection device of any of paragraphs A1-A2, wherein the device has one or more of:
 an injector-receipt configuration, in which the injector is received by and secured to the injection assembly;
 a ready configuration, in which the eye-contacting surface of the alignment guide is engaged with the surface of the patient's eye and the alignment portion of the alignment guide is aligned with the predetermined visible aspect of the patient's eye;
 a range of translation configurations, in which the injector is being translated by the activator;
 a translated configuration, in which the injector has been translated the translation distance and the dispensing conduit has been inserted into the patient's eye;
 a range of plunging configurations, in which the injectant is being dispensed from the injector by the activator;
 a dispensed configuration, in which the injectant has been dispensed from the injector by the activator;
 a range of retraction configurations, in which the injector is being retracted by the activator; and
 a retracted configuration, in which the injector has been retracted by the activator.

A4 The intravitreal injection device of any of paragraphs A1-A3, wherein the activator is further adapted to retract the injector a retraction distance relative to the injection assembly after the dispensing of the injectant from the injector.

A5 The intravitreal injection device of paragraph A4, wherein the retraction distance is equal to the translation distance.

A6 The intravitreal injection device of any of paragraphs A4-A5, wherein the activator is adapted to automatically retract the injector the retraction distance upon the injectant being dispensed from the injector.

A7 The intravitreal injection device of any of paragraphs A4-A6, wherein the activator includes a biased retraction mechanism.

A8 The intravitreal injection device of any of paragraphs A4-A7, wherein the activator is adapted to automatically retract the injector the retraction distance upon the user disengaging the user actuation mechanism.

A9 The intravitreal injection device of any of paragraphs A1-A8, wherein the injector is a syringe that includes a barrel for receiving a volume of injectant, the dispensing conduit includes a needle coupled to the barrel for delivering the injectant from the syringe, and a plunger slidingly received in the barrel for selective dispensing of the injectant from the barrel via the needle; and wherein the injection assembly includes a barrel-translator and a plunger-translator, wherein responsive to the user engaging the user actuation mechanism, the activator is adapted to automatically and sequentially first, translate the barrel-translator to translate the syringe the translation distance and then second, translate the plunger-translator a plunging distance relative to the barrel to dispense the injectant from the barrel via the needle.

A10 The intravitreal injection device of paragraph A9, wherein the syringe includes a finger flange extending from the barrel, and wherein the barrel translator is adapted to engage the finger flange when the syringe is received by the injection assembly.

A11 The intravitreal injection device of any of paragraphs A9-A10, wherein the injection assembly is adapted to selectively receive and secure thereto syringes having different configurations.

A12 The intravitreal injection device of paragraph A11, wherein at least one of the barrel-translator and the plunger-translator are selected from a plurality of translators configured to mate with a predetermined one or more of the syringes having different configurations, and wherein the plurality of translators are adapted to be selectively received and released by the injection assembly so that the intravitreal injection device can be configured by the user for use with a selected syringe from the syringes having different configurations.

A13 The intravitreal injection device of any of paragraphs A11-A12, wherein the syringes having different configurations include syringes having different volumes of barrels.

A14 The intravitreal injection device of any of paragraphs A11-A13, wherein the syringes having different configurations include syringes of different manufacturers.

A15 The intravitreal injection device of any of paragraphs A11-A14, wherein the syringes having different configurations include syringes having differently configured finger flanges.

A16 The intravitreal injection device of any of paragraphs A11-A15, wherein the syringes having different configurations include syringes having differently configured plungers.

A17 The intravitreal injection device of any of paragraphs A11-A16, wherein the syringes having different configurations include syringes having different lengths of needles.

A18 The intravitreal injection device of any of paragraphs A9-A17, wherein the activator includes a cam system, wherein the barrel-translator includes a barrel-cam adapted to translate the barrel in response to the user engaging the user actuation mechanism, and wherein the plunger-translator includes a plunger-cam adapted to translate the plunger in response to the user engaging the user actuation mechanism after the barrel-cam translates the barrel.

A19 The intravitreal injection device of any of paragraphs A9-A17, wherein the activator includes a linkage system including a plurality of links, wherein the barrel-translator includes a barrel-link adapted to translate the barrel in response to the user engaging the user actuation mechanism, and wherein the plunger-translator includes a plunger-link adapted to translate the plunger in response to the user engaging the user actuation mechanism after the barrel-link translates the barrel.

A20 The intravitreal injection device of any of paragraphs A9-A17, wherein the activator includes a concentric screw system that includes an internally threaded casing adapted to rotate in response to the user engaging the user actuation mechanism, wherein the barrel-translator includes an externally threaded barrel-driver in threaded engagement with the casing, and wherein the plunger-translator includes an externally threaded plunger-driver in threaded engagement with the casing, wherein when the casing rotates in a first direction a first predetermined number of rotations, the barrel-driver and the plunger-driver translate the syringe the translation distance, and wherein when the casing rotates in the first direction a second predetermined number of rotations beyond the first predetermined number of rotations, the plunger-driver translates the plunger relative to the barrel to dispense the injectant.

A21 The intravitreal injection device of any of paragraphs A9-A17, wherein the activator includes a rack and pinion system including an input lever, wherein the barrel-translator includes a barrel-pinion and a barrel-rack, wherein the barrel-pinion is adapted to engage the barrel-rack for only a portion of its rotational movement, wherein the plunger-translator includes a plunger-pinion and a plunger-rack in engagement with the plunger-pinion, wherein the plunger-pinion and the barrel-pinion are coupled to each other and rotate together in response to rotational movement of the input lever, wherein when the input lever is pivoted a first predetermined angle, the barrel-rack and the plunger-rack translate the syringe the translation distance, and wherein when the input lever is pivoted a second predetermined angle beyond the first predetermined angle, the plunger-rack translates the plunger relative to the barrel to dispense the injectant.

A22 The intravitreal injection device of any of paragraphs A9-A21, wherein the activator is electrically powered.

A23 The intravitreal injection device of any of paragraphs A9-A21, wherein the activator is not electrically powered.

A24 The intravitreal injection device of any of paragraphs A9-A23, wherein the activator is at least partially pneumatically controlled.

A25 The intravitreal injection device of any of paragraphs A9-A24, wherein the activator is at least partially hydraulically controlled.

A26 The intravitreal injection device of any of paragraphs A1-A25, wherein the eye-contacting surface is shaped to conform to the surface of the patient's eye.

A27 The intravitreal injection device of any of paragraphs A1-A25, wherein the eye-contacting surface is adapted to conform to the surface of the patient's eye.

A28 The intravitreal injection device of any of paragraphs A1-A27, wherein the alignment guide is selected from a plurality of alignment guides having different configurations, with each configuration being configured for use with a selected injector from a plurality of injectors having different configurations.

A29 The intravitreal injection device of any of paragraphs A1-A28, wherein the alignment guide is coupled to the injection assembly.

A30 The intravitreal injection device of paragraph A29, wherein the alignment guide is removably coupled to the injection assembly.

A31 The intravitreal injection device of any of paragraphs A29-A30, wherein the alignment guide includes a detector adapted to detect if a force of the alignment guide against the surface of the patient's eye is at least a threshold force.

A32 The intravitreal injection device of any of paragraphs A29-A30, wherein the injection assembly further includes a detector supported by the housing and adapted to detect if a force of the alignment guide against the surface of the patient's eye is at least a threshold force.

A33 The intravitreal injection device of any of paragraphs A29-A32, wherein the injection assembly further includes a detector coupled to at least one of the housing, the user actuation mechanism, and the activator, wherein the detector is adapted to detect if a force of the alignment guide against the surface of the patient's eye is at least a threshold force.

A34 The intravitreal injection device of any of paragraphs A31-A33, wherein the detector is adapted to restrict activation of the activator if the force of the alignment guide against the surface of the patient's eye is not at least the threshold force.

A35 The intravitreal injection device of any of paragraphs A31-A34, wherein the detector is adapted to restrict translation of the injector if the force of the alignment guide against the surface of the patient's eye is not at least the threshold force.

A36 The intravitreal injection device of any of paragraphs A31-A35, wherein the detector is adapted to restrict dispensing of the injectant if the force of the alignment guide against the surface of the patient's eye is not at least the threshold force.

A37 The intravitreal injection device of any of paragraphs A31-A36, wherein the detector is in communication with the user actuation mechanism, and the user actuation mechanism is adapted to restrict actuation of the activator if the force of the alignment guide against the surface of the patient's eye is not at least the threshold force.

A38 The intravitreal injection device of any of paragraphs A34-A37, wherein the detector is in mechanical communication with the user actuation mechanism.

A39 The intravitreal injection device of any of paragraphs A34-A38, wherein the detector is in electrical communication with the user actuation mechanism.

A40 The intravitreal injection device of any of paragraphs A31-A36, wherein the detector is in communication with the activator and the activator is adapted to restrict translation of the injector and dispensing of the injectant if the force of the alignment guide against the surface of the patient's eye is not at least the threshold force.

A41 The intravitreal injection device of paragraph A40, wherein the detector is in mechanical communication with the activator.

A42 The intravitreal injection device of any of paragraphs A40-A41, wherein the detector is in electrical communication with the activator.

A43 The intravitreal injection device of any of paragraphs A29-A42, wherein the injection assembly further includes a notification mechanism adapted to notify the user when the force of the alignment guide against the surface of the patient's eye is not above the threshold force.

A44 The intravitreal injection device of any of paragraphs A29-A42, wherein the injection assembly further includes a notification mechanism adapted to notify the user when the force of the alignment guide against the surface of the patient's eye is above the threshold force.

A45 The intravitreal injection device of any of paragraphs A43-A44, wherein the notification mechanism includes a visual indicator.

A46 The intravitreal injection device of any of paragraphs A44-A45, wherein the notification mechanism includes an audible indicator.

A47 The intravitreal injection device of any of paragraphs A1-A28, wherein the alignment guide is adapted to be coupled to the injector.

A48 The intravitreal injection device of paragraph A47, wherein the alignment guide is adapted to be removably and replaceably coupled to the injector.

A49 The intravitreal injection device of any of paragraphs A47-A48, wherein at least a portion of the alignment guide is adapted to translate relative to the injector when the activator translates the injector.

A50 The intravitreal injection device of any of paragraphs A47-A49, in combination with the injector, wherein the alignment guide is coupled to the injector.

A51 The intravitreal injection device of any of paragraphs A1-A50, wherein the alignment guide is a sterilized alignment guide that is configured to be disposed of after use.

A52 The intravitreal injection device of any of paragraphs A1-A51, wherein the alignment guide includes a base that includes the eye-contacting surface and an edge that defines the alignment portion.

A53 The intravitreal injection device of paragraph 52, wherein the base further includes two prongs, between which the dispensing conduit of the injector translates when the activator translates the injector.

A54 The intravitreal injection device of any of paragraphs A52-A53, wherein the base is generally U-shaped.

A55 The intravitreal injection device of any of paragraphs A52-A53, wherein the base is generally V-shaped.

A56 The intravitreal injection device of any of paragraphs A52-A55, wherein the base is generally fork shaped.

A57 The intravitreal injection device of paragraph A52, wherein the base defines a passage, through which the dispensing conduit of the injector translates when the activator translates the injector.

A58 The intravitreal injection device of paragraph A57, wherein the passage has an enclosed inner perimeter.

A59 The intravitreal injection device of any of paragraphs A1-A51, wherein the alignment guide includes a resiliently flexible band that includes the eye-contacting surface and an edge that defines the alignment portion, and wherein the resiliently flexible band is adapted to at least partially conform to the surface of the patient's eye when the alignment guide is positioned against the patient's eye and the injection assembly is translated toward the patient's eye by the user.

A60 The intravitreal injection device of paragraph A59, wherein the resiliently flexible band is adapted to restrict translation of the injection assembly toward the patient's eye after a predetermined operating distance away from the patient's eye.

A61 The intravitreal injection device of any of paragraphs A59-A60, wherein the resiliently flexible band is adapted to exert an opposing force that biases the injection assembly away from the patient's eye and to restrict translation of the injection assembly toward the patient's eye beyond a predetermined operating distance away from the patient's eye.

A62 The intravitreal injection device of paragraph A61, wherein the opposing force prevents translation of the injection assembly toward the patient's eye beyond the predetermined operating distance away from the patient's eye.

A63 The intravitreal injection device of any of paragraphs A59-A62, wherein the resiliently flexible band is further adapted to dampen translation of the injection assembly relative to the patient's eye.

A64 The intravitreal injection device of any of paragraphs A1-A63, wherein the alignment guide includes indicia adapted to facilitate placement of the alignment portion relative to the predetermined visible aspect of the patient's eye.

A65 The intravitreal injection device of paragraph A64, wherein the indicia includes a scale of distance increments.

A66 The intravitreal injection device of any of paragraphs A1-A65, wherein the alignment portion is contoured to correspond to the predetermined visible aspect of the patient's eye.

A67 The intravitreal injection device of paragraph A66, wherein the alignment portion is contoured to correspond to the edge of the patient's iris.

A68 The intravitreal injection device of any of paragraphs A1-A67, wherein the alignment guide includes an eyelid engagement flange adapted to restrict the patient's eyelid from covering the predetermined injection site on the patient's eye when the user has positioned the eye-contacting surface against the surface of the patient's eye.

A69 The intravitreal injection device of any of paragraphs A1-A68 wherein the alignment guide includes an eyelid engagement flange adapted to restrict the patient's eyelid from obstructing the user's sight of the predetermined visible aspect of the patient's eye when the user has positioned the eye-contacting surface against the surface of the patient's eye.

A70 The intravitreal injection device of any of paragraphs A1-A68, wherein the alignment guide includes an eyelid engagement flange adapted to restrict the patient's eyelid from obstructing the user's sight of the alignment portion when the user has positioned the eye-contacting surface against the surface of the patient's eye.

A71 The intravitreal injection device of any of paragraphs A1-A70, wherein at least a portion of the alignment guide is translucent.

A72 The intravitreal injection device of any of paragraphs A1-A71 wherein at least a portion of the alignment guide is transparent, and optionally wherein the device further includes a light source adapted to illuminate the alignment guide without shining light directly into the patient's eye.

A73 The intravitreal injection device of any of paragraphs A1-A72, wherein the alignment guide is adapted to selectively suction the eye-contacting surface against the surface of the patient's eye when the eye-contacting surface is engaged with the surface of the patient's eye.

A74 The intravitreal injection device of paragraph A73, wherein the alignment guide includes a conduit extending from the eye-contacting surface to the injection assembly, and wherein the injection assembly includes a suction mechanism supported by the housing and adapted to selectively apply a suction to the conduit to thereby suction the eye-contacting surface against the surface of the patient's eye when the eye-contacting surface is engaged with the surface of the patient's eye.

A75 The intravitreal injection device of any of paragraphs A1-A72, wherein the alignment guide includes a body that defines an internal volume and a passage through which the dispensing conduit of the injector translates when the injector is translated by the activator, wherein the body further defines a port through the eye-contacting surface and open to the internal volume, and wherein the injection assembly includes a suction mechanism supported by the housing and adapted to selectively apply a suction to the internal volume to thereby suction the eye-contacting surface against the surface of the patient's eye when the eye-contacting surface is engaged with the surface of the patient's eye.

A76 The intravitreal injection device of any of paragraphs A1-A75, wherein the alignment guide includes one or more gripping regions disposed on the eye-contacting surface and adapted to restrict relative movement between the patient's eye and the alignment guide when the eye-contacting surface is engaged with the surface of the patient's eye.

A77 The intravitreal injection device of paragraph A76, wherein the one or more gripping regions include one or more protrusions.

A78 The intravitreal injection device of any of paragraphs A1-A77, wherein the injection assembly further includes a light source supported by the housing and adapted to illuminate at least the injection site on the surface of the patient's eye.

A79 The intravitreal injection device of any of paragraphs A1-A78, further comprising:
a stabilization device adapted to couple the injection assembly to a foundation, wherein the stabilization device is adapted to facilitate the user's manipulation of the housing to position the injector adjacent to the patient's eye.

A80 The intravitreal injection device of paragraph A79, wherein the stabilization device is further adapted to retain the housing in a selected position when the user selectively releases the housing.

A81 The intravitreal injection device of any of paragraphs A79-A80, wherein the stabilization device is further adapted to dampen translation of the housing.

A82 The intravitreal injection device of any of paragraphs A79-A81, wherein the stabilization device includes a mechanical arm.

A83 The intravitreal injection device of any of paragraphs A79-A82, wherein the foundation is a stationary foundation.

A84 The intravitreal injection device of any of paragraphs A79-A82, wherein the foundation is a portable foundation.

A85 The intravitreal injection device of any of paragraphs A79-A84, wherein the foundation includes a patient examination chair.

A86 The intravitreal injection device of any of paragraphs A79-A84, wherein the foundation includes a patient examination table.

A87 The intravitreal injection device of any of paragraphs A79-A86, wherein the stabilization device includes the foundation.

A88 The intravitreal injection device of any of paragraphs A1-A87, wherein the injection assembly further includes a notification mechanism adapted to notify a user of the intravitreal injection device of a predetermined criterion associated with the intravitreal injection device.

A89 The intravitreal injection device of paragraph A88, wherein the notification mechanism is adapted to visually notify the user of the predetermined criterion.

A90 The intravitreal injection device of any of paragraphs A88-A89, wherein the notification mechanism is adapted to audibly notify the user of the predetermined criterion.

A91 The intravitreal injection device of any of paragraphs A88-A90, wherein the predetermined criterion includes a status of the translation of an injector by the activator.

A92 The intravitreal injection device of any of paragraphs A88-A91, wherein the predetermined criterion includes a status of the dispensing of the injectant from the injector by the activator.

A93 The intravitreal injection device of any of paragraphs A88-A92, wherein the predetermined criterion includes a force of the engagement of the eye-contacting surface of the alignment guide against the surface of the patient's eye.

A94 The intravitreal injection device of any of paragraphs A88-A93, wherein the predetermined criterion includes a relative force between the alignment guide and the injection assembly.

A95 The intravitreal injection device of any of paragraphs A1-A94, wherein the injectant includes a pharmaceutical.

A96 The intravitreal injection device of paragraph A95, wherein the pharmaceutical is adapted to treat macular degeneration.

A97 The intravitreal injection device of any of paragraphs A1-A96, wherein the injectant includes at least one of LUCENTIS® brand pharmaceutical and AVASTIN® brand pharmaceutical, or a pharmaceutical of similar or identical composition.

A98 The intravitreal injection device of any of paragraphs A1-A97, wherein the injectant includes a liquid.

A99 The intravitreal injection device of any of paragraphs A1-A98, wherein the injectant includes a solid.

A100 The intravitreal injection device of any of paragraphs A1-A99, wherein the injectant includes one or more solid pellets.

A101 The intravitreal injection device of any of paragraphs A1-A100, wherein the injectant includes a gas.

A102 The intravitreal injection device of any of paragraphs A1-A101, wherein the injectant includes sulfur hexafluoride.

A103 The intravitreal injection device of any of paragraphs A1-A102, wherein housing is adapted to be grasped and manipulated using a single hand of the user to position the injector adjacent to a patient's eye when the injector is secured to the injection assembly, and further wherein the user-actuation mechanism is adapted to be actuated by the user's single hand upon positioning of the injector.

A104 An intravitreal injection device, comprising:
an injection assembly adapted to selectively receive an injector containing an injectant and having a dispensing conduit and secure the injector to the injection assembly in a defined orientation, wherein the injection assembly is further adapted to selectively release the injector from the injection assembly, and wherein the injection assembly comprises:
  a housing adapted to be selectively grasped by a user and manipulated to position the injector adjacent to a patient's eye when the injector is secured to the injection assembly;
  a user actuation mechanism supported by the housing and adapted to be engaged by the user; and
  an activator supported by the housing, wherein responsive to the user engaging the user actuation mechanism, the activator is adapted to automatically and sequentially first, reconfigure the intravitreal injection device from an injector-receipt configuration, in which the injector is received by and secured to the injection assembly, to a translated configuration, in which the activator has translated the injector a translation distance, and second, reconfigure the intravitreal injection device from the translated configuration to a dispensed configuration, in which the activator has dispensed the injectant from the injector; and
an alignment guide supported relative to the housing (e.g., coupled to the injection assembly or adapted to be coupled to the injector), wherein the alignment guide includes an eye-contacting surface oriented to extend across a region of a surface of the patient's eye when the user positions the injector adjacent to the patient's eye, and an alignment portion adapted to be aligned with a predetermined visible aspect of the patient's eye when the eye-contacting surface is engaged with the surface of the patient's eye, wherein the alignment portion is in a predetermined position relative to a predetermined injection site on the surface of the patient's eye through which the dispensing conduit of the injector will pass when the injector is received by and secured to the injection assembly and translated by the activator.

A105 The intravitreal injection device of paragraph A104, further defined by any of paragraphs A2-A103.

A106 An intravitreal injection device, comprising:
means for selectively (i) receiving an injector containing an injectant and having a dispensing conduit, (ii) securing the injector in a defined orientation relative to the intravitreal injection device, and (iii) releasing the injector, wherein the means for selectively receiving, securing, and releasing comprises:
  means for positioning the injector adjacent to a patient's eye;
  means for receiving user input; and
  means for automatically, in response to the user input, sequentially first, translating the injector a translation distance and second, dispensing the injectant from the injector; and
means for engaging a surface of the patient's eye and providing a reference for a user to position the intravitreal injection device in a desired position relative to a visible aspect of the patient's eye.

A107 The intravitreal injection device of paragraph A106, further defined by any of the paragraphs A1-A104.

A108 A method of injecting an injectant into a patient's eye using the intravitreal injection device of any of paragraphs A1-A107.

A109 A method of treating macular degeneration and/or of treating a detached retina using the intravitreal injection device of any of paragraphs A1-A107 to inject the injectant into the vitreous cavity of the patient's eye.

A110 The use of the intravitreal injection device of any of paragraphs A1-A107.

A111 The use of the intravitreal injection device of any of paragraphs A1-A107 to treat macular degeneration.

A112 An injection or extraction device, comprising structure of the intravitreal injection device of any of paragraphs A1-A104.

A113 An injection device, comprising:
an injection assembly adapted to selectively receive an injector containing an injectant and having a dispensing conduit and secure the injector to the injection assembly in a defined orientation, wherein the injection assembly is further adapted to selectively release the injector from the injection assembly, and wherein the injection assembly comprises:
  a housing adapted to be selectively grasped by a user and manipulated to position the injector adjacent to a patient's body when the injector is secured to the injection assembly;
  a user actuation mechanism supported by the housing and adapted to be engaged by the user; and
  an activator supported by the housing, wherein responsive to the user engaging the user actuation mechanism, the activator is adapted to automatically and sequentially first, translate the injector a translation distance relative to the injection assembly and then second, dispense the injectant from the injector; and
an alignment guide supported relative to the housing (e.g., coupled to the injection assembly or adapted to be coupled to the injector), wherein the alignment guide includes a body-contacting surface oriented to extend across a region of a surface of the patient's body when the user positions the injector adjacent to the patient's body, and an alignment portion adapted to be aligned with a predetermined visible aspect of the patient's body when the body-contacting surface is engaged with the surface of the patient's body, wherein the alignment portion is in a predetermined position relative to a predetermined injection site on the surface of the patient's body through which the dispensing conduit of the injector will pass when the injector is received by and secured to the injection assembly and translated by the activator.

A114 The injection device of paragraph A113, further defined by the structure recited in any of paragraphs A2-A103, wherein the patient's eye is interpreted be the patient's body, such as a soft tissue of the patient's body, and the eye-contacting surface is interpreted to be the body-contacting portion.

A115 A method of injecting an injectant into a patient's body using the injection device of any of paragraphs A113-A114.

A116 The method of paragraph 115 performed by a user using only one of the user's hands.

A117 The use of the injection device of any of paragraphs A113-A114.

B1 A method for injecting an injectant into a patient's eye by an intravitreal injection device, the method comprising:
receiving, by the intravitreal injection device, an injector having a dispensing conduit for dispensing the injectant into the patient's eye;
engaging, by the intravitreal injection device, a surface of the patient's eye;
translating, by the intravitreal injection device, the injector a translation distance so that the dispensing conduit penetrates the patient's eye to a predetermined depth; and
after the translating, dispensing, by the intravitreal injection device, the injectant from the injector into the patient's eye via the dispensing conduit.

B2 The method of paragraph B1, further comprising, prior to the translating, receiving a user input, wherein the translating and the dispensing are responsive to the user input.

B3 The method of paragraph B1, further comprising:
after the engaging and prior to the translating and the dispensing, detecting, by the intravitreal injection device, a force of engagement against the surface of the patient's eye;
wherein the translating includes translating the injector the translation distance only if the force is at least a threshold force.

B4 The method of paragraph B3, wherein the dispensing includes dispensing the injectant only if the force exceeds the threshold force.

B5 The method of any of paragraphs B1-B4, further comprising:
preventing the translating and the dispensing if a force of engagement of the intravitreal injection device against the surface of the patient's eye is not at least a threshold force.

B6 The method of any of paragraphs B1-B5, further comprising:
notifying, by the intravitreal injection device, a user of the intravitreal injection device of a predetermined criterion associated with the intravitreal injection device.

B7 The method of paragraph B6, wherein the notifying includes visually notifying the user of the predetermined criterion.

B8 The method of any of paragraphs B6-B7, wherein the notifying includes audibly notifying the user of the predetermined criterion.

B9 The method of any of paragraphs B6-B8, further comprising:
after the engaging and prior to the translating and the dispensing, detecting, by the intravitreal injection device, a force of engagement against the surface of the patient's eye;
wherein the notifying includes notifying the user if the force of engagement against the surface of the patient's eye is at least a threshold force.

B10 The method of any of paragraphs B6-B9, further comprising:
after the engaging and prior to the translating and the dispending, detecting, by the intravitreal injection device, a force of engagement against the surface of the patient's eye;
wherein the notifying includes notifying the user if the force of engagement against the surface of the patient's eye is not at least a threshold force.

B11 The method of any of paragraphs B6-B10, wherein the predetermined criterion includes a status of the translating.

B12 The method of any of paragraphs B6-B11, wherein the predetermined criterion includes a status of the dispensing.

B13 The method of any of paragraphs B1-B12, further comprising:
after the dispensing, retracting, by the intravitreal injection device, the injector a retraction distance so that the dispensing conduit exits the patient's eye.

B14 The method of paragraph B13, further comprising:
notifying, by the intravitreal injection device, a user of the intravitreal injection device of a status of the retracting.

B15 The method of any of paragraphs B1-B14, wherein the injector is a syringe that includes a barrel for receiving a volume of the injectant, the dispensing conduit coupled to the barrel for delivering the injectant from the syringe, and a plunger slidingly received in the barrel for selective dispensing of the injectant from the barrel via the dispensing conduit.

B16 The method of paragraph B15, wherein the syringe includes a finger flange extending from the barrel.

B17 The method of any of paragraphs B1-B16, wherein the injector is a first injector, the patient is a first patient, and the method further comprises:
after the dispensing, releasing, by the intravitreal injection device, the first injector; and
after the releasing:
receiving, by the intravitreal injection device, a second injector having a dispensing conduit for dispensing the injectant into a second patient's eye;
engaging, by the intravitreal injection device, a surface of the second patient's eye;
translating, by the intravitreal injection device, the second injector a translation distance so that the dispensing conduit of the second injector penetrates the second patient's eye to a predetermined depth; and
after the translating the second injector, dispensing, by the intravitreal injection device, the injectant from the second injector into the second patient's eye via the dispensing conduit of the second injector.

B18 The method of paragraph B17, wherein the second injector has a different configuration than the first injector.

B19 The method of paragraph B18, wherein the second injector has a different injectant capacity than the first injector.

B20 The method of any of paragraphs B17-B19, wherein the second injector is of a different manufacturer than the first injector.

B21 The method of any of paragraphs B1-B20, further comprising:
illuminating, by intravitreal injection device, the surface of the patient's eye, B22 The method of any of paragraphs B1-B21, further comprising:
restricting, by the intravitreal injection device, the patient's eyelid from covering a site of the dispensing conduit's penetration of the patient's eye.

B23 The method of any of paragraphs B1-B22, further comprising:
restricting, by the intravitreal injection device, the patient's eyelid from obstructing a line of sight of a user of the intravitreal injection device to a predetermined visible aspect of the patient's eye.

B24 The method of any of paragraphs B1-B23, further comprising:
restricting, by the intravitreal injection device, the patient's eyelid from obstructing a line of sight of a user of the intravitreal injection device to a predetermined portion of the intravitreal injection device.

B25 The method of any of paragraphs B1-B24, wherein the engaging includes gripping the surface of the patient's eye to stabilize the intravitreal injection device in a selected position against the surface of the patient's eye.

B26 The method of paragraph B25, wherein the gripping includes applying a suction to the surface of the patient's eye.

B27 The method of any of paragraphs B1-B26, further comprising:
restricting, by the intravitreal injection device, movement of the intravitreal injection device after a user has positioned the intravitreal injection device in a desired position.

B28 The method of any of paragraphs B1-B27, further comprising:
damping, by the intravitreal injection device, movements of the intravitreal injection device.

B29 The method of any of paragraphs B1-B28, further comprising:
retaining, by the intravitreal injection device, the intravitreal injection device in a user selected position.

B30 The method of any of paragraphs B1-B29, further comprising:
facilitating, by the intravitreal injection device, translation of the intravitreal injection device by a user.

B31 The method of any of paragraphs B1-B30, further comprising:
prior to the engaging, receiving, by the intravitreal injection device, an alignment guide that includes an eye-contacting surface and an alignment portion adapted to be positioned adjacent to a predetermined visible aspect of the patient's eye, wherein the alignment portion is a predetermined distance from a position through which the injector will pass during the translating step; and
releasing, by the intravitreal injection device, the alignment guide;
wherein the engaging includes engaging the surface of the patient's eye with the eye-contacting surface of the alignment guide.

B32 The method of any of paragraphs B1-B31, wherein the injectant includes a pharmaceutical.

B33 The method of paragraph B32, wherein the pharmaceutical is adapted to treat macular degeneration.

B34 The method of any of paragraphs B1-B33, wherein the injectant includes at least one of LUCENTIS® brand pharmaceutical and AVASTIN® brand pharmaceutical, or a pharmaceutical of similar or identical composition.

B35 The method of any of paragraphs B1-B34, wherein the injectant includes a liquid.

B36 The method of any of paragraphs B1-B35, wherein the injectant includes a solid.

B37 The method of any of paragraphs B1-B36, wherein the injectant includes one or more solid pellets.

B38 The method of any of paragraphs B1-B37 wherein the method is performed by the device of any of paragraphs A1-A107 and A112-A114.

B39 The method of any of paragraphs B1-B38, wherein the patient's eye is interpreted to be the patient's body, such as a soft tissue of the patient's body.

C1 A method of injecting an injectant into a patient's eye utilizing an intravitreal injection device, the method comprising:
securing an injector to the intravitreal injection device;
positioning the intravitreal injection device adjacent to the patient's eye;
aligning an alignment guide of the intravitreal injection device with a predetermined visible aspect of the patient's eye;
positioning the intravitreal injection device so that the eye-contacting surface of the alignment guide engages a surface of the patient's eye; and
actuating the intravitreal injection device so that the intravitreal injection device automatically and sequentially first, translates a dispensing conduit of the injector into the patient's eye and then second, dispenses the injectant into the patient's eye.

C2 The method of paragraph C1, wherein the actuating is performed by a single motion of the user.

C3 The method of paragraph C2, wherein the actuating includes engaging a button or a switch.

C4 The method of any of paragraphs C1-C3, further comprising:
after the actuating, removing the dispensing conduit from the patient's eye.

C5 The method of paragraph C4, wherein the removing includes removing the dispensing conduit after the intravitreal injection device has indicated that the injectant was dispensed from the injector.

C6 The method of any of paragraphs C1-C5, further comprising:
after the actuating, removing the injector from the intravitreal injection device.

C7 The method of paragraph C6, further comprising:
after the removing, disposing of the injector.

C8 The method of any of paragraphs C6-C7, wherein the injector is a first injector and the method further comprises:
after the removing:
securing a second injector to the intravitreal injection device;
positioning the intravitreal injection device adjacent to a second patient's eye;
aligning the alignment guide of the intravitreal injection device with a predetermined visible aspect of the second patient's eye;
positioning the intravitreal injection device so that an eye-contacting surface of the alignment guide engages a surface of the second patient's eye; and
actuating the intravitreal injection device so that the intravitreal injection device translates a dispensing conduit of the second injector into the second patient's eye and dispenses the injectant into the second patient's eye.

C9 The method of paragraph C8, wherein the second injector has a different configuration than the first injector.

C10 The method of paragraph C9, wherein the second injector has a different injectant capacity than the first injector.

C11 The method of any of paragraphs C9-C10, wherein the second injector is of a different manufacturer than the first injector.

C12 The method of any of paragraphs C1-C11, further comprising:
prior to the securing, inserting the injectant into the injector.

C13 The method of any of paragraphs C1-C12, wherein the injector is a syringe that includes a barrel for receiving a volume of the injectant, the dispensing conduit is coupled to the barrel for delivering the injectant from the syringe, and a plunger is slidingly received in the barrel for selective dispensing of the injectant from the barrel via the dispensing conduit, C14 The method of paragraph C13, wherein the syringe includes a finger flange extending from the barrel.

C15 The method of any of paragraphs C1-C14, wherein the actuating includes actuating the intravitreal injection device after the intravitreal injection device has indicated that a force of the alignment guide against the surface of the patient's eye is at least a threshold force.

C16 The method of any of paragraphs C1-C15, further comprising:
prior to the positioning, securing the alignment guide to the intravitreal injection device; and
after the actuating, removing the alignment guide from the intravitreal injection device.

C17 The method of paragraph C6, further comprising:
after the removing, disposing of the alignment guide.

C18 The method of any of paragraphs C1-C17, wherein the alignment guide is a presterilized alignment guide.

C19 The method of any of paragraphs C1-C18, wherein the injectant includes a pharmaceutical.

C20 The method of paragraph C19, wherein the pharmaceutical is adapted to treat macular degeneration.

C21 The method of any of paragraphs C1-C20, wherein the injectant includes at least one of LUCENTIS® brand pharmaceutical and AVASTIN® brand pharmaceutical, or a pharmaceutical of similar or identical composition.

C22 The method of any of paragraphs C1-C21, wherein the injectant includes a liquid.

C23 The method of any of paragraphs C1-C22, wherein the injectant includes a solid.

C24 The method of any of paragraphs C1-C23, wherein the injectant includes one or more solid pellets.

C25 The method of any of paragraphs C1-C24, wherein the method utilizes the device of any of paragraphs A1-A107 and A112-A114.

C26 The method of any of paragraphs C1-C25, wherein the patient's eye is interpreted to be the patient's body, such as a delicate tissue of the patient's body.

In the event that the provisional patent application incorporated by reference herein defines or uses a term in a manner inconsistent with the non-incorporated disclosure of the present application, the non-incorporated disclosure of the present application shall control, and the term or terms as used in the incorporated provisional application only control with respect to the provisional patent application.

The disclosure set forth above encompasses multiple distinct inventions with independent utility. While each of these inventions has been disclosed in its preferred form, the specific examples thereof as disclosed and illustrated herein are not to be considered in a limiting sense, as numerous variations are possible. The present disclosure includes all novel and non-obvious combinations and subcombinations of the various elements, features, functions, properties, methods, and/or steps disclosed herein. Similarly, where any disclosure, including the claims below, recite "a" or "a first" element, step of a method, or the equivalent thereof, such disclosure or claim should be understood to include one or more such elements or steps, neither requiring nor excluding two or more such elements.

Inventions embodied in various combinations and subcombinations of features, functions, elements, properties, methods, and/or steps may be claimed through presentation of amended claims or new claims in a related application. Such new claims, whether they are directed to a different invention or directed to the same invention, whether different, broader, narrower, or equal in scope to the original claims, are also regarded as included within the subject matter of the present disclosure.

INDUSTRIAL APPLICABILITY

The devices according to the present disclosure are applicable to the opthalmology field, and are specifically applicable to devices for the injection and/or extraction of a substance to and/or from a patient's eye.

The invention claimed is:

1. An intravitreal injection device, comprising:
an injection assembly adapted to selectively receive an injector containing an injectant and having a dispensing conduit and secure the injector to the injection assembly in a defined orientation, wherein the injection assembly is further adapted to selectively release the injector from the injection assembly, and wherein the injection assembly comprises:
a housing adapted to be selectively grasped by a user and manipulated to position the injector adjacent to a patient's eye when the injector is secured to the injection assembly;
a user actuation mechanism supported by the housing and adapted to be engaged by the user; and
an activator supported by the housing, wherein responsive to the user engaging the user actuation mechanism, the activator is adapted to automatically and sequentially first, translate the injector a translation distance relative to the injection assembly and then second, dispense the injectant from the injector; and
an alignment guide supported relative to the housing, wherein the alignment guide includes an eye-contacting surface oriented to extend across a region of a surface of the patient's eye when the user positions the injector adjacent to the patient's eye, and an alignment portion adapted to be aligned with a predetermined visible aspect of the patient's eye when the eye-contacting surface is engaged with the surface of the patient's eye, wherein the alignment portion is in a predetermined position relative to a predetermined injection site on the surface of the patient's eye through which the dispensing conduit of the injector will pass when the injector is received by and secured to the injection assembly and translated by the activator.

2. The intravitreal injection device of claim 1, wherein the activator is further adapted to retract the injector a retraction distance relative to the injection assembly after the dispensing of the injectant from the injector.

3. The intravitreal injection device of claim 1,
wherein the injector is a syringe that includes a barrel for receiving a volume of injectant and a finger flange extending from the barrel, the dispensing conduit includes a needle coupled to the barrel for delivering the injectant from the syringe, and a plunger slidingly received in the barrel for selective dispensing of the injectant from the barrel via the needle; and
wherein the injection assembly includes a barrel-translator and a plunger-translator, wherein responsive to the user engaging the user actuation mechanism, the activator is adapted to automatically and sequentially first, translate the barrel-translator to translate the syringe the translation distance and then second, translate the plunger-translator a plunging distance relative to the barrel to dispense the injectant from the barrel via the needle.

4. The intravitreal injection device of claim 3, wherein the injection assembly is adapted to selectively receive and secure thereto syringes having different configurations.

5. The intravitreal injection device of claim 3, wherein the activator includes a concentric screw system that includes an internally threaded casing adapted to rotate in response to the user engaging the user actuation mechanism, wherein the barrel-translator includes an externally threaded barrel-driver in threaded engagement with the casing, and wherein the plunger-translator includes an externally threaded plunger-driver in threaded engagement with the casing, wherein when the casing rotates in a first direction a first predetermined number of rotations, the barrel-driver and the plunger-driver translate the syringe the translation distance, and wherein when the casing rotates in the first direction a second predetermined number of rotations beyond the first predetermined number of rotations, the plunger-driver translates the plunger relative to the barrel to dispense the injectant.

6. The intravitreal injection device of claim 3, wherein the activator includes a rack and pinion system including an input lever, wherein the barrel-translator includes a barrel-pinion and a barrel-rack, wherein the barrel-pinion is adapted to engage the barrel-rack for only a portion of its rotational movement, wherein the plunger-translator includes a plunger-pinion and a plunger-rack in engagement with the plunger-pinion, wherein the plunger-pinion and the barrel-pinion are coupled to each other and rotate together in response to rotational movement of the input lever, wherein when the input lever is pivoted a first predetermined angle, the barrel-rack and the plunger-rack translate the syringe the translation distance, and wherein when the input lever is pivoted a second predetermined angle beyond the first predetermined angle, the plunger-rack translates the plunger relative to the barrel to dispense the injectant.

7. The intravitreal injection device of claim 1, wherein the alignment guide is selected from a plurality of alignment guides having different configurations, with each configuration being configured for use with a selected injector from a plurality of injectors having different configurations.

8. The intravitreal injection device of claim 1, wherein the alignment guide is coupled to the injection assembly.

9. The intravitreal injection device of claim 8, wherein the alignment guide includes a detector adapted to detect if a force of the alignment guide against the surface of the patient's eye is at least a threshold force.

10. The intravitreal injection device of claim 9, wherein the detector is adapted to restrict activation of the activator if the force of the alignment guide against the surface of the patient's eye is not at least the threshold force.

11. The intravitreal injection device of claim 1, wherein the alignment guide includes a base that includes the eye-contacting surface and an edge that defines the alignment portion, and wherein the base further includes two prongs, between which the dispensing conduit of the injector translates when the activator translates the injector.

12. The intravitreal injection device of claim 1, wherein the alignment guide includes a resiliently flexible band that includes the eye-contacting surface and an edge that defines the alignment portion, and wherein the resiliently flexible band is adapted to at least partially conform to the surface of the patient's eye when the alignment guide is positioned against the patient's eye and the injection assembly is translated toward the patient's eye by the user.

13. The intravitreal injection device of claim 1, wherein the alignment portion is contoured to correspond to the predetermined visible aspect of the patient's eye.

14. The intravitreal injection device of claim 1, wherein the alignment guide includes an eyelid engagement flange adapted to restrict the patient's eyelid from covering the predetermined injection site on the patient's eye when the user has positioned the eye-contacting surface against the surface of the patient's eye.

15. The intravitreal injection device of claim 1, wherein the alignment guide includes one or more gripping regions disposed on the eye-contacting surface and adapted to restrict relative movement between the patient's eye and the alignment guide when the eye-contacting surface is engaged with the surface of the patient's eye.

16. The intravitreal injection device of claim 1, further comprising:
 a stabilization device adapted to couple the injection assembly to a foundation, wherein the stabilization device is adapted to facilitate the user's manipulation of the housing to position the injector adjacent to the patient's eye and to retain the housing in a selected position when the user selectively releases the housing.

17. The intravitreal injection device of claim 1, wherein the injection assembly further includes a notification mechanism adapted to notify a user of the intravitreal injection device of a predetermined criterion associated with the intravitreal injection device.

18. The intravitreal injection device of claim 17, wherein the predetermined criterion includes a status of the translation of an injector by the activator.

19. The intravitreal injection device of claim 17, wherein the predetermined criterion includes a status of the dispensing of the injectant from the injector by the activator.

20. The intravitreal injection device of claim 17, wherein the predetermined criterion includes a force of the engagement of the eye-contacting surface of the alignment guide against the surface of the patient's eye.

21. An intravitreal injection device, comprising:
 means for selectively (i) receiving an injector containing an injectant and having a dispensing conduit, (ii) securing the injector in a defined orientation relative to the intravitreal injection device, and (iii) releasing the injector, wherein the means for selectively receiving, securing, and releasing comprises:
 means for positioning the injector adjacent to a patient's eye;
 means for receiving user input; and
 means for automatically, in response to the user input, sequentially first, translating the injector a translation distance and second, dispensing the injectant from the injector; and
 means for engaging a surface of the patient's eye and providing a reference for a user to position the intravitreal injection device in a desired position relative to a visible aspect of the patient's eye.

22. The intravitreal injection device of claim 1, wherein the alignment guide is adapted to selectively suction the eye-contacting surface against the surface of the patient's eye when the eye-contacting surface is engaged with the surface of the patient's eye.

23. The intravitreal injection device of claim 22, wherein the alignment guide includes a conduit extending from the eye-contacting surface to the injection assembly, and wherein the injection assembly includes a suction mechanism supported by the housing and adapted to selectively apply a suction to the conduit to thereby suction the eye-contacting surface against the surface of the patient's eye when the eye-contacting surface is engaged with the surface of the patient's eye.

24. The intravitreal injection device of claim 1, wherein the alignment guide includes a body that defines an internal volume and a passage through which the dispensing conduit of the injector translates when the injector is translated by the activator, wherein the body further defines a port through the eye-contacting surface and open to the internal volume, and wherein the injection assembly includes a suction mechanism supported by the housing and adapted to selectively apply a suction to the internal volume to thereby suction the eye-contacting surface against the surface of the patient's eye when the eye-contacting surface is engaged with the surface of the patient's eye.

* * * * *